United States Patent
Lash et al.

(10) Patent No.: US 11,944,432 B1
(45) Date of Patent: Apr. 2, 2024

(54) FLEXIBLE OXIMETER SENSOR PANEL

(75) Inventors: Robert E. Lash, Redwood City, CA (US); Jimmy Jian-min Mao, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 2420 days.

(21) Appl. No.: 12/326,491

(22) Filed: Dec. 2, 2008

(51) Int. Cl.
| | |
|---|---|
| A61B 5/1455 | (2006.01) |
| A61B 5/00 | (2006.01) |
| A61B 5/024 | (2006.01) |
| A61B 90/00 | (2016.01) |

(52) U.S. Cl.
CPC ...... *A61B 5/14552* (2013.01); *A61B 5/02427* (2013.01); *A61B 5/1455* (2013.01); *A61B 5/447* (2013.01); *A61B 5/6801* (2013.01); *A61B 5/6843* (2013.01); *A61B 2090/065* (2016.02); *A61B 2562/0247* (2013.01); *A61B 2562/043* (2013.01); *A61B 2562/046* (2013.01); *A61B 2562/063* (2013.01); *A61B 2562/066* (2013.01)

(58) Field of Classification Search
CPC ........................................ A61B 5/1455–14558
USPC ................ 600/310, 322, 323, 344, 340, 587
See application file for complete search history.

(56) References Cited

U.S. PATENT DOCUMENTS

| | | | | |
|---|---|---|---|---|
| 5,069,213 A | * | 12/1991 | Polczynski | A61B 5/14552 600/323 |
| 5,253,656 A | * | 10/1993 | Rincoe | A61B 5/1036 600/595 |
| 5,309,908 A | * | 5/1994 | Friedman et al. | 600/322 |
| 5,678,544 A | | 10/1997 | De Lonzor et al. | |
| 5,891,021 A | * | 4/1999 | Dillon et al. | 600/310 |
| 6,122,042 A | * | 9/2000 | Wunderman et al. | 356/73 |
| 6,516,209 B2 | | 2/2003 | Cheng et al. | |
| 6,520,834 B1 | * | 2/2003 | Marshall | B24B 37/04 451/10 |
| 6,587,703 B2 | | 7/2003 | Cheng et al. | |
| 6,600,940 B1 | * | 7/2003 | Fein | A61B 5/14552 600/323 |
| 7,355,688 B2 | | 4/2008 | Lash et al. | |
| 7,396,331 B2 | * | 7/2008 | Mack | A61B 5/024 600/300 |
| 7,512,432 B2 | * | 3/2009 | Zocchi | 600/347 |
| 7,764,982 B2 | * | 7/2010 | Dalke et al. | 600/310 |
| 8,011,041 B2 | * | 9/2011 | Hann | 5/652.1 |
| 2004/0143172 A1 | * | 7/2004 | Fudge et al. | 600/344 |
| 2007/0123756 A1 | * | 5/2007 | Kitajima et al. | 600/300 |

(Continued)

OTHER PUBLICATIONS

Ogando, Joseph et al., "Fabrics Get Smart", EDN, Aug. 3, 2006, pp. 39-44.

*Primary Examiner* — Devin B Henson
*Assistant Examiner* — H. Q. Nguyen
(74) *Attorney, Agent, or Firm* — Aka Chan LLP

(57) ABSTRACT

Methods and devices monitor oxygen saturation levels in tissue. According to one aspect of the invention, a device is a sensor panel comprising a flexible substrate and a plurality of oximeter sensor units coupled to the substrate. In another aspect of the invention, the device is a sensor panel comprising a flexible substrate and a plurality of oximeter sensor units and a plurality of pressure sensors coupled to the substrate. Embodiments of the invention can be used to simultaneously measure oxygen saturation levels in many locations of a large tissue. Embodiments of the invention can be applied in diagnosing a medical condition involving a large tissue area where the oxygen saturation level is unstable.

8 Claims, 13 Drawing Sheets

(56) References Cited

U.S. PATENT DOCUMENTS

| | | | |
|---|---|---|---|
| 2008/0015424 A1* | 1/2008 | Bernreuter | A61B 5/14551 600/323 |
| 2008/0106792 A1 | 5/2008 | Lash et al. | |
| 2008/0108886 A1 | 5/2008 | Lash et al. | |
| 2008/0214953 A1* | 9/2008 | Hashimshony | A61B 5/0059 600/562 |
| 2008/0312517 A1* | 12/2008 | Genoe | A61B 5/14551 600/323 |
| 2009/0243833 A1* | 10/2009 | Huang et al. | 340/505 |

* cited by examiner

FLEXIBLE OXIMETER SENSOR PANEL

BACKGROUND OF THE INVENTION

This invention relates to the field of medical devices and more specifically to oximeters. Oximeters are noninvasive medical devices that can be used to measure oxygen saturation of tissues in patients. Human tissues include a variety of light-absorbing and light-scattering chromophores which can interact with electromagnetic waves transmitted thereto and traveling therethrough. For example, human tissues include deoxygenated and oxygenated hemoglobins which are the most dominant chromophores in the spectrum range of 600 nanometers to 900 nanometers. Light-absorption and light-scattering patterns differ significantly between deoxygenated and oxygenated hemoglobins at certain wavelengths of light.

An oximeter uses this difference to determine oxygen saturation of tissues. Assessing the patient's oxygenation state, both systematic and cellular level, is important as it is an indicator of the state of the patient's health. Thus, it is often used in clinical settings, such as in emergency rooms and hospitals, during surgery and recovery, where it is suspected that the patient's tissue oxygenation state is unstable.

While a number of different oximeters are on the market today, many oximeters measure the oxygenation saturation of a very small area in a tissue. In some clinical settings, it is not practical to use an oximeter with such a small scanning head, particularly when a tissue to be examined is large. For example, it will be cumbersome and labor intensive to measure the oxygen saturation of the entire abdomen or back with an oximeter with a small scanning head.

Oximeters also typically have a sensor head that is hard and rigid. These oximeters can be sometimes awkward to use. For example, if a doctor wishes to explore a large contoured surface of a body, a patient will suffer discomfort when a rigid and flat sensor head of an oximeter is pressed against the patient's body. Moreover, there may not be proper contact between the contoured surface of the body and the hard, rigid sensor head of the oximeter. This may result in inaccurate readings of the oxygen saturation of tissues.

Moreover, in dealing with a large tissue, a doctor may be uncertain what area of the tissue is compromised in terms of oxygenation. For example, a patient who suffered a stroke can be generally immobile and can be on a prolonged bed rest. The patient is at risk of developing pressure ulcers, because pressure ulcers develop in the skin and its underlying tissues when soft tissues are compressed between bony prominences and contact surfaces. Pressure ulcers can also develop when there is friction or shearing force, causing erosion and tissue ischemia. When tissues to be monitored are large (e.g., a body surface being compressed onto a bed), it may be difficult for a doctor to determine which area is suffering from tissue ischemia and is compromised in terms of oxygenation.

In spite of modern advances in diagnosis and treatment, pressure ulcers develop quickly, persist tenaciously and heal very slowly. An estimated 1.3 to 3 million patients in the United States have pressure ulcers and incidences are higher in elderly patients, who are in hospitals or long-term care facilities. While a caretaker can visually inspect the patient's body for pressure ulcers, it may be desirable to have a monitoring system that can help diagnose the development of pressure ulcers at an early stage before they actually erupt in the skin.

Accordingly, there is a need to improve monitoring systems such as oximeter sensors and sensor systems for determining oxygenation state of a tissue. The present invention addresses these and other needs.

BRIEF SUMMARY OF THE INVENTION

Embodiments of the invention include sensor panels, sensor panel arrays, systems, and methods for using these devices and systems to measure oxygen saturation of a tissue at multiple locations.

In one embodiment, a sensor panel includes a flexible substrate and a number of oximeter sensor units connected to the flexible substrate, where each oximeter sensor unit includes a first source structure and a first detector structure. A source structure provides light to be transmitted into a tissue. A detector structure collects or detects light that is scattered and reflected from the tissue. In some embodiments, there are two or more source structures and detector structures in the oximeter sensor unit.

In another embodiment, a sensor panel includes a flexible substrate and a number of oximeter sensor units and a number of pressure sensors connected to the flexible substrate. In this embodiment, one can read both pressure applied to the tissue and oxygen saturation of the tissue at multiple locations.

In another embodiment, a sensor panel array includes two or more sensor panels tiled together so that oxygen saturation measurements can be made from a large tissue area.

In another embodiment, a system includes a sensor panel and a system unit which includes a processor, a memory, and an output unit, operatively connected together.

In another embodiment, a method includes applying to a tissue, a sensor panel including a flexible substrate and a number of oximeter sensor units connected to the flexible substrate, determining oxygen saturation values at locations of the tissue corresponding to positions of the oximeter sensor units, and determining if any of the oxygen saturation values is below a predetermined safety value.

In another embodiment, a method includes applying to a tissue, a sensor panel including a flexible substrate and a number of oximeter sensor units and a number of pressure sensors connected to the flexible substrate, determining oxygen saturation of and pressure applied to various locations of the tissue, and determining whether to provide an output signal.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1A:
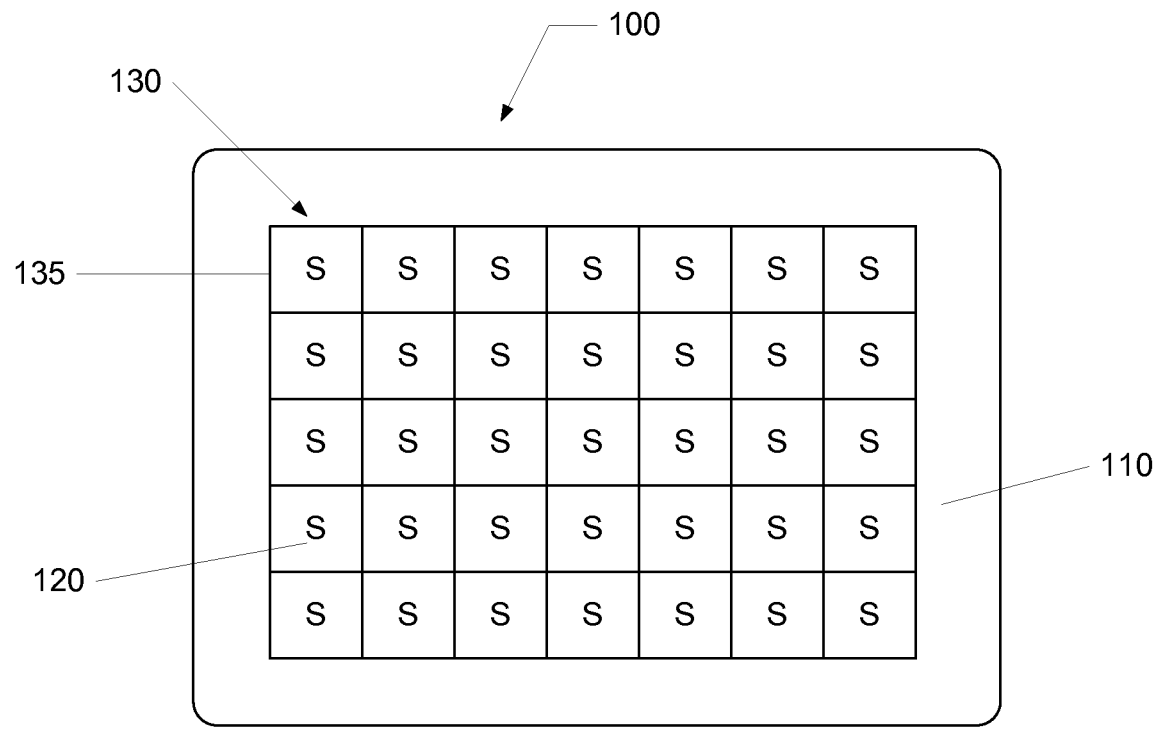
FIG. 1A shows an example of a sensor panel including a flexible substrate and oximeter sensor units connected to the flexible substrate, where the oximeter sensor units are arranged in a form of a matrix.

Embodiments of the invention include sensor panels, sensor panel arrays, systems, and methods for determining oxygen saturation of a target tissue at multiple locations. In embodiments of the invention, a sensor panel includes a flexible substrate and oximeter sensor units connected to the flexible substrate. These sensor panels can be made of any suitable shape and size so that they can simultaneously measure oxygen saturation of a large tissue at various locations. If desired, two or more sensor panels can be tiled together to make a sensor panel array that can monitor even a whole body.

In embodiments of the invention, a sensor panel includes a flexible substrate, such as a fabric. In an implementation, the flexible substrate is soft so that the sensor panel has good feel against the skin. Because of its flexibility, the present sensor panel and sensor panel array are easy to apply and drape over a contoured surface of a large tissue or body. For example, a flexible sensor panel can be applied over an abdomen or back, and it conforms and drapes over contoured surfaces of these body parts. A better contact between the tissue and the present sensor panel can result in a more accurate reading of the tissue oxygen saturation.

In some embodiments, a sensor panel also has pressure sensors connected to a flexible substrate. The pressure sensors can measure pressure applied from a tissue to the sensor panel. For example, when a sensor panel is applied to the entire back, the sensor panel may have good contact with an upper portion of the back, while the sensor panel may not have good contact with a lower portion of the back that is curved inward. Therefore, the pressure sensors can be used to determine if there is good contact between the tissue and the sensor panel. Based on pressure readings from the sensor panel, a user can determine if oxygen saturation measurements from certain body parts are accurate.

Embodiments of the invention can be used in a wide variety of applications. One application is in monitoring oxygen saturation of a tissue that has a contoured or curved surface. Another application is in monitoring oxygen saturation of a relatively large tissue at multiple locations simultaneously. Another application in clinical area is in monitoring patients at risk of developing pressure ulcers.

Pressure ulcers develop in the skin and its underlying tissues when soft tissues are compressed between bony prominences and contact surfaces. Pressure ulcers can also develop when there are frictional forces (e.g., rubbing against clothing or bedding) or shearing forces (which develop when skin clings to surfaces), which can cause erosion and tissue ischemia. Patients with cognitive impairment, immobility, or both are at higher risk of developing pressure ulcers. When tissues to be monitored are large (e.g., a body surface being compressed onto a bed), it may be difficult for a doctor to determine which area is suffering from tissue ischemia and is compromised in terms of oxygenation.

In embodiments of the invention, a sensor panel (or a sensor panel array including multiple sensor panels) can be incorporated into a bed sheet or a garment to monitor oxygenation saturation of a patient's body contacting the bed sheet or the garment. This allows a doctor to monitor oxygen saturation of a large area of the patient's body being compressed onto a bed. Since the present sensor panels can measure oxygen saturation of tissues under the skin, the doctor can monitor the oxygenation state of tissues underlying the skin and can assess the patient's risk for developing pressure ulcers at an earlier stage, before they erupt in the skin.

While the present invention can be used to diagnose pressure ulcer development, there are many other applications. Embodiments of the invention can be applied in any situation when it is suspected that the oxygenation state of a tissue is compromised.

Embodiments of the invention provide for a number of advantages. For example, embodiments of the invention can be applied to relatively large areas of tissue and can simultaneously measure oxygen saturation from multiple locations of the larger tissue area. Flexibility of embodiments of the invention also provides good contact between a contoured surface of the tissue area and oximeter sensor units, thereby resulting in a more accurate reading of the tissue oxygen saturation. Incorporating pressure sensors in embodiments of the invention further assists in determining whether there is good contact between the tissue and the oximeter sensor units. Embodiments of the invention can be applied in diagnosing any conditions involving unstable oxygenation of tissues.

Examples of embodiments of the invention are illustrated using figures and are described below. The figures described herein are used to illustrate embodiments of the invention, and are not in any way intended to limit the scope of the invention.

I. Sensor Panel

FIGS. 1A through 1D illustrate various examples of a sensor panel having different shapes and oximeter sensor unit arrangements.

FIG. 1A shows a sensor panel 100 including a flexible substrate 110 and oximeter sensor units 120 (represented by "S") connected to the flexible substrate 110. In the sensor panel 100, the oximeter sensor units 120 are arranged in an array, in a form of a matrix 130. The matrix 130 is generally rectangular in shape and typically has a number of rows and columns of pixel elements 135, at which each of the oximeter sensor units 120 is located. As shown in FIG. 1A, each of the oximeter sensor units 120 is positioned in each pixel element 135 of the matrix 130. When the sensor panel 100 is applied to a tissue, the oxygen saturation can be measured at each location of the tissue that is in contact with each oximeter sensor unit of the sensor panel. Thus, the total area of the tissue that is scanned by the sensor panel approximately corresponds to the area of the matrix.

In FIG. 1A, the sensor panel has five rows and seven columns of oximeter sensor units 120 in a form of a matrix. However, a matrix can vary in size and shape. In one embodiment, a sensor panel can have one hundred rows and one hundred columns of oximeter sensor units in a form of matrix. In another embodiment, a sensor panel can have two rows and two columns of oximeter sensor units. In yet another embodiment, any a sensor panel can have any number of rows between two and one hundred and any number of columns between two and one hundred of oximeter sensor units. There can be any number of sensors per unit area such as 1, 2, 3, 5, 6, 8, or 20 sensors per square inch, per square foot, per square centimeter, or per square meter.

The shape of the matrix depends on the end use of a sensor panel. For example, if it is desired to measure oxygen saturation of a tissue that is narrow in width but long in length, the oximeter sensor units can be arranged in a matrix that has, e.g., two rows and thirty columns. If it is desired to measure oxygen saturation of a larger tissue, then the oximeter sensor units can be arranged in a matrix having, e.g., thirty rows and thirty columns.

The size of the pixel element 135 in a matrix can also vary in its size, depending on, among other things, the depth of a tissue that a user wishes to examine the oxygenation state. A pixel element can be of any suitable size, as long as it can accommodate the size of an oximeter sensor unit. For example, each pixel element can have a dimension of about 30 by 30 millimeters, about 20 by 20 millimeters, about 10 by 10 millimeters, about 5 by 5 millimeters, or about 2 by 2 millimeters. Each pixel element need not be in the shape of a square but can be in another shape, such as a rectangle. For example, each pixel element can have a dimension of about 30 by 10 millimeters, about 20 by 10 millimeters, 30 millimeters by 5 millimeters, or 20 by 10 millimeters. A larger pixel element can accommodate a larger oximeter sensor unit, while a smaller pixel element can accommodate a smaller oximeter sensor unit.

In some embodiments, the size of the pixel element can be coextensive with the size of oximeter sensor units. In other words, each oximeter sensor unit can occupy the entire space of pixel element and may be touching neighboring oximeter sensor units. In this embodiment, the size of pixel elements described above is equivalent to the size of oximeter sensor units. In other embodiments, the size of oximeter sensor units may be smaller than the size of pixel element. In this embodiment, neighboring oximeter sensor units may not be physically touching one another.

Although FIG. 1A illustrates an embodiment where the oximeter sensor units "S" 120 occupy each pixel element 135 of the matrix 130, the oximeter sensor units may not occupy every the pixel elements in the matrix. The oximeter sensor units can be distributed and grouped in any suitable manner depending on the end use of the sensor panel. For example, depending on the nature of a tissue to be examined, the oximeter sensor units can be concentrated in certain areas and distributed more sparely in another area in the sensor panel. By distributing and placing the oximeter sensor units only in the desired or necessary pixel elements, the production cost of sensor panels can be reduced.

Figure 1B:
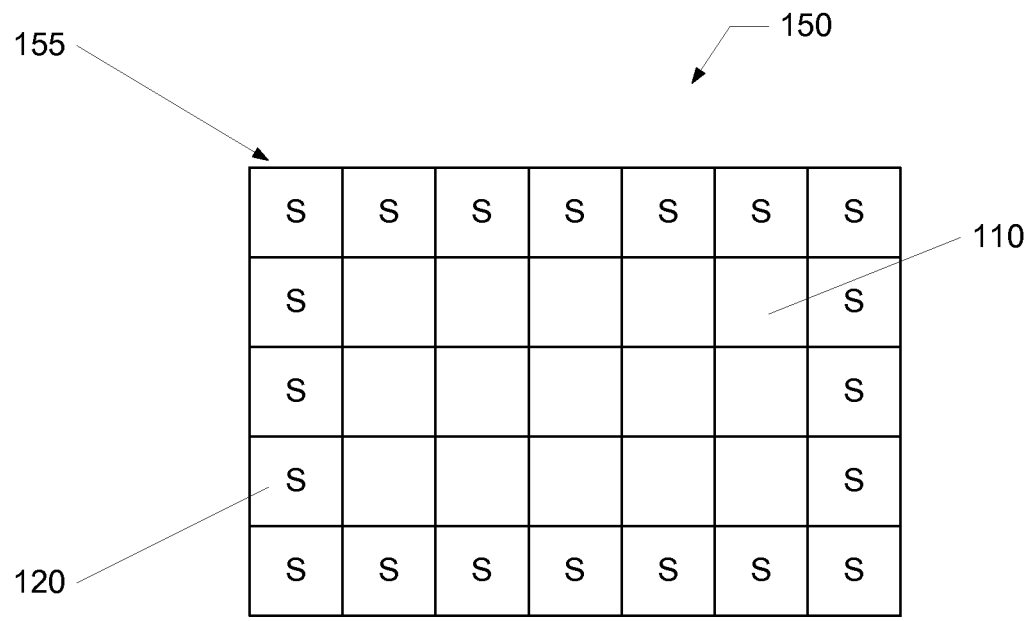
FIG. 1B shows an example of a sensor panel, where the oximeter sensor units are unevenly distributed and are more concentrated in the outer portion of a matrix.

FIG. 1B illustrates an example where oximeter sensor units do not occupy every the pixel elements of the matrix. FIG. 1B also illustrates that a sensor panel may not have a margin of a flexible substrate surrounding a matrix. Rather, the size of a matrix may be coextensive with the size of a flexible substrate. In FIG. 1B, a sensor panel 150 includes a flexible substrate 110 connected to oximeter sensor units 120, where the oximeter sensor units are not located in the center of the matrix 155, but located only in the outer pixel elements of the matrix. In this embodiment, oximeter sensor units can be located at the outer most boundary of the sensor panel. This type of sensor panel can be useful if a tissue to be examined is such that only the outer edges of the tissue are of importance in terms of oxygenation and the middle area is not informative.

Figure 1C:
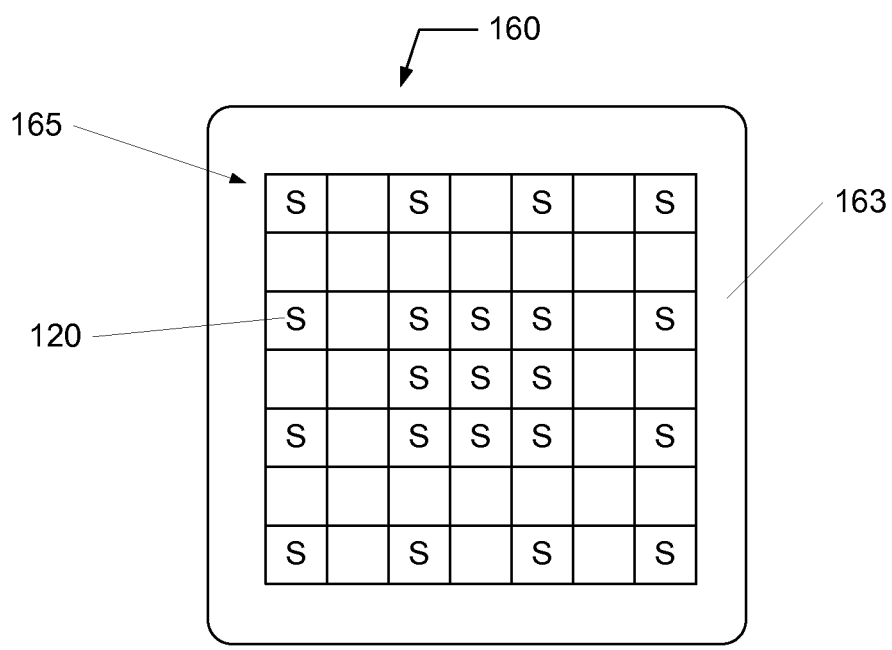
FIG. 1C shows an example of a sensor panel, where the oximeter sensor units are more concentrated in the center of the sensor panel.

FIG. 1C illustrates another example where the oximeter sensor units do not occupy every the pixel elements of the matrix. In FIG. 1C, a sensor panel 160 includes a flexible substrate 163 connected with oximeter sensor units 120, where the oximeter sensor units are more concentrated in the middle of the matrix 165, and are more sparsely distributed in the outer pixel elements of the matrix 165. As shown in FIG. 1C, the oximeter sensor units 120 do not occupy every consecutive pixel elements, but occupy every other pixel elements in the outer pixel elements of the matrix 165. This type of uneven distribution of oximeter sensor units can be useful when it is desired to obtain a lot of information from one focal area of a tissue, but sparse information from its surrounding tissue areas. For example, it may be desirable to obtain many oxygen saturation readings from a tissue area containing clusters of lymph nodes, but it may be sufficient to obtain sparse readings from other surrounding areas of the lymph nodes. Thus, the grouping and concentration of oximeter sensor units in a sensor panel may depend on the nature of a tissue to be scanned and examined.

FIGS. 1A, 1B, and 1C illustrate some examples of oximeter sensor unit distribution. The distribution pattern is not limited to those shown in these figures. For example, the oximeter sensor units can be distributed in any suitable or desired pattern, such as a wavy line, a zigzag line, an X-pattern, a concentric circular pattern, or a spiral pattern. The pattern and distribution of oximeter sensor units approximately correspond to locations of a tissue that is scanned for oxygen saturation.

Figure 1D:
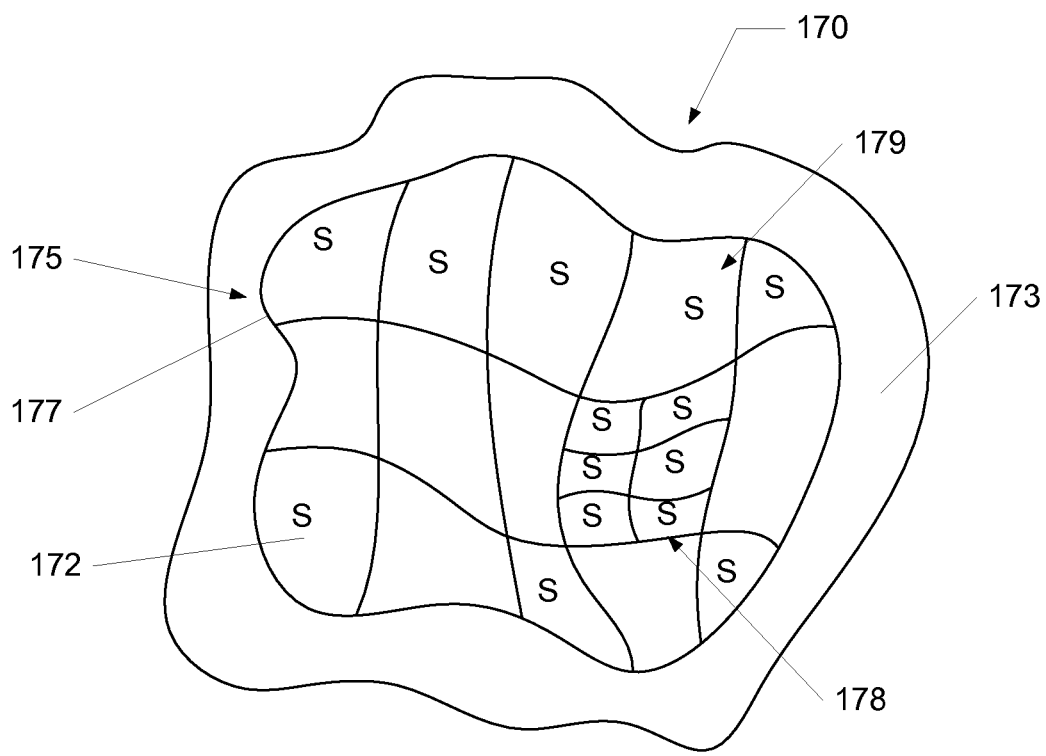
FIG. 1D shows an example of a sensor panel, where the oximeter sensor units are arranged in an irregular grid, in which rows are formed from nonstraight lines that are not parallel to one another and columns are formed from non-straight lines that are not parallel to one another.

FIG. 1D illustrates an example of a sensor panel where oximeter sensor units are not arranged in a form of a matrix. Rather, the sensor panel 170 includes oximeter sensor units 172 that are arranged in an irregular lattice 175, which has rows formed from nonstraight (e.g., curved, angled, irregular, bent, indirect, nonlinear, curly, twisted, spiraled, or winding) lines that are not parallel to one another and columns formed from nonstraight lines that are not parallel to one another. Thus, the irregular grid 175 has pixel elements 177 that are not shaped as a square or rectangle. Rather, each pixel element 177 typically forms a quadrilateral having four vertices, where a first line drawn through two adjacent vertices and a second line drawn through the other two adjacent vertices are not parallel. When a body or tissue surface to be examined is highly contoured, it may be more informative to use a sensor panel including oximeter sensor units in an irregular grid that mimics the topography of the body or tissue surface.

Furthermore, the oximeter sensor units may be unevenly distributed throughout the sensor panel. As shown in FIG. 1D, oximeter sensor units represented by "S" occupy some of the pixel elements 177 in the sensor panel 170, and some of the pixel elements 177 are empty. Moreover, the sensor panel has at least two regions of different densities of oximeter sensor units. As shown in FIG. 1D, a region 178 has a higher density of oximeter sensor units and a region 179 has a lower density of oximeter sensor units compared to the region 178. For example, the region 178 may have about four to six oximeter sensor units per four square centimeters, where the region 179 may have less than two oximeter sensor units per four square centimeters. Depending on the nature of a tissue to be examined, it may be advantageous to use a sensor panel having oximeter sensor units distributed nonuniformly or asymmetrically in an irregular grid.

Many variations of oximeter sensor unit distribution and numbers can be implemented in embodiments of the invention. Depending on the size of a matrix or an irregular grid, a sensor panel can have a total of 6, 8, 10, 15, 20, 25, 30, 35, 40, 50, 60, 70, 80, 90, 100, 160, or 200 oximeter sensor units or any other number. The overall density of oximeter sensor units in a matrix or in an irregular grid can also vary. For example, a matrix or an irregular grid can have about 0.1, 0.2, 0.5, 0.8, 1, 2, 5 oximeter sensor units per square centimeters of the matrix or the irregular grid, or any number. Moreover, oximeter sensor units can be distributed such that two oximeter sensor units that are located farthest apart from each other in the sensor panel can be about 2, 4, 5, 6, 8, 10, 16, 20, 30, 40 or 50 centimeters apart or any other number.

It is illustrated in FIGS. 1A through 1D that a flexible substrate is larger than the size of a matrix (i.e., an area occupied by oximeter sensor units in a sensor panel). This size difference may assist a user in handling the sensor panel without having to touch the scanning surface of the oximeter sensor units. However, this size difference is not essential to embodiments of the invention, and the flexible substrate and the matrix can be co-extensive in size as shown in FIG. 1B. The FIGS. 1A through 1D illustrate some example of sensor panels having different shape, size, and distribution pattern of oximeter sensor units. Other variations, while not illustrated, are within the scope of the present invention.

In embodiments of the invention, the flexible substrates can be made of any suitable material. Examples of a flexible substrate include a fabric or textile, a foam sheet, a polymeric sheet, and an elastomeric sheet. Depending on the end application of a sensor panel, it is desirable to use a flexible substrate that is soft and comfortable against a body and that is easy to drape over a contoured surface of the body. It is also desirable to have a flexible substrate that is breathable and nonsticky against the body. In some embodiments, it may be desirable to have a flexible substrate that is elastic or stretchable.

In one embodiment of the invention, a fabric can be used as a flexible substrate in a sensor panel. A fabric can be in any form—knitted, woven, or nonwoven. A fabric can be made from synthetic fibers (e.g., nylon, polyester, or Lycra®), natural fibers (e.g., cotton, wool, or silk), or a combination of both. A fabric can also comprise fibers that have additional functions, such as electrically conductive fibers or optical fibers. It is desirable that the selected fabric is durable and washable, allowing a sensor panel including the fabric to be incorporated into another structure, such as a garment or a bed sheet. It is desired that a sensor panel having a fabric as a flexible substrate can withstand at least about 5, 10, 20, 30, or 50 washing cycles.

A flexible substrate can also be a monolithic layer or a multilayered structure. In one embodiment, a flexible substrate is a multilayered fabric, where each layer has a different function (e.g., electrically conductive or electrically insulating). In another embodiment, a flexible substrate can be a multilayered structure with pockets for placing oximeter sensor units.

In a sensor panel, there are different ways that oximeter sensor units can be positioned with respect to a flexible substrate. In one embodiment, the oximeter sensor units can be placed on a top surface of the flexible substrate (i.e., the surface that will be facing and contacting a tissue). In another embodiment, oximeter sensor units can be embedded or integrated in the flexible substrate. Since oximeter sensor units and their connectors are embedded (i.e., enclosed) in the flexible substrate, the sensor panel is more comfortable against human skin. In this embodiment, light transmission properties of the oximeter sensor units may be reduced by the flexible substrate. The reduction in light transmission properties can be taken into account, and oxygen saturation readings from a tissue can be calibrated accordingly.

A variety of coupling elements can be used to couple or attach oximeter sensor units to a flexible substrate. In some embodiments, the oximeter sensor units are bonded to the flexible substrate using an adhesive. Any suitable adhesive (e.g., fabric glue) can be used as long as it does not alter the optical or electrical properties of the sensor panel. If a fabric is used as a flexible substrate, oximeter sensor units can be sewn into the fabric or can be weaved into the fabric as a part of the fabric structure.

II. Oximeter Sensor Units

An oximeter sensor unit measures oxygen saturation of a tissue. Each oximeter sensor unit includes at least one source structure and at least one detector structure. A source structure is a structure in the oximeter sensor unit that provides light that can be transmitted into a tissue. The source structure can generate the light, or it can be a structural component that transmits the light generated elsewhere (e.g., from an upstream source). A detector structure is a structure in the oximeter sensor unit that detects light (or that is a structural component of the detection process) which is scattered and reflected from the tissue.

Typically, a source structure emits light of one or more specific wavelengths in visible or infrared range suitable for monitoring oxygen saturation of a tissue. For example, a source structure can provide light having a wavelength from about 600 nanometers to about 900 nanometers. In one embodiment, a source structure provides light having a wavelength of 690 nanometers, and a detector structure can detect the light of the same wavelength. In another embodiment, a source structure provides light having a wavelength of 830 nanometers, and the detector structure can detect the light of the same wavelength. In some embodiments, the same source structure can provide light of two or more wavelengths, and the same detector structure can detect the light of the same wavelengths.

In one embodiment, a source structure can be a laser or light emitting diode (LED) that emits a light of a specific wavelength suitable to monitor oxygen saturation. A detector structure can be a photodiode (e.g., a PN diode, a PIN diode, or an avalanche diode) that detects the light transmitted and reflected from a tissue, after the source structure emits the light into the tissue. In an oximeter sensor unit, both LEDs and photodiodes are located at the scanning surface of the oximeter sensor unit. These LEDs and photodiodes can then be electrically connected to a system unit which will be described below. In this embodiment, since the light is generated next to the tissue surface and subsequently detected at the tissue surface, there is less attenuation of a signal.

In another embodiment, a source structure is an opening in an oximeter sensor unit (at its scanning surface) with an optical fiber inside, which is connected to an emitter located elsewhere (e.g., system unit). Likewise, a detector structure is an opening in an oximeter sensor unit (at its scanning surface) with an optical fiber inside, which is connected to a detector located elsewhere. The optical fibers from each oximeter sensor unit are then connected to either an emitter or a detector which may be located in a system unit.

FIGS. 2A through 2H show various configurations of source structures and detector structures in an oximeter sensor unit. Each figure shows a particular opening pattern. The openings in the figures can be either source structures or detector structures, and they may be referred to herein as an opening or openings in FIGS. 2A through 2H. While the figures show only some examples of opening patterns, other opening patterns may be used with embodiments of the invention.

Figure 2A:
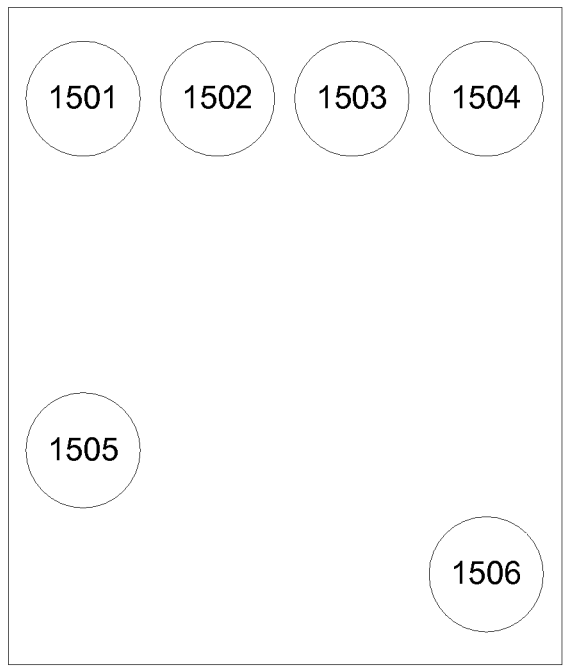
FIG. 2A shows an oximeter sensor unit opening pattern (i.e., source structure and detector structure arrangements) where one oximeter sensor unit opening is aligned asymmetrically with respect to the other oximeter sensor unit openings.

FIG. 2A shows a specific implementation of an oximeter sensor unit. This oximeter sensor unit has six openings 1501-1506. Openings 1501-1504 are arranged in a line closer to a first edge of the oximeter sensor unit, while openings 1505 and 1506 are arranged closer to a second edge, which is opposite the first edge. In fact, opening 1506 is closer than opening 1505 to the second edge. In an implementation, the first edge is distal to the second edge, which is closer to a cable attached to the sensor panel.

In this implementation, the oximeter sensor unit has a rectangular shape, but the oximeter sensor unit may have any shape such a trapezoid, triangle, dodecagon, octagon, hexagon, square, circle, or ellipse. An oximeter sensor unit of any shape or form can incorporate the sensor openings in the pattern shown and described.

In one implementation, openings 1501-1504 are detector structures while openings 1505 and 1506 are source structures. However, in other implementations, there can be one or more detector structures, two or more detector structures, one or more source structures, or two or more source structures. For example, there may be three detector structures and three source structures or one detector structures and five source structures.

In FIG. 2A, the openings are positioned asymmetrically such that a line drawn through openings 1501-1504 is not parallel to a line drawn through openings 1505 and 1506. However, a line drawn through openings 1501 and 1505 is parallel to a line through openings 1504 and 1506. Additionally, the distance between openings 1501 and 1504 is shorter than the distance between openings 1505 and 1506.

Thus, the distance between openings 1501 and 1505 does not equal the distance between openings 1501 and 1506; the distance between openings 1502 and 1505 does not equal the distance between openings 1503 and 1505; and the distance between openings 1503 and 1505 does not equal the distance between openings 1504 and 1506.

In a specific implementation, a distance between openings 1501 and 1504 is five millimeters. A distance between each of the openings 1501, 1502, 1503, and 1504 is 5/3 millimeters. A distance between 1501 and 1505 is five millimeters. A diameter of an opening is one millimeter.

Figure 2B:
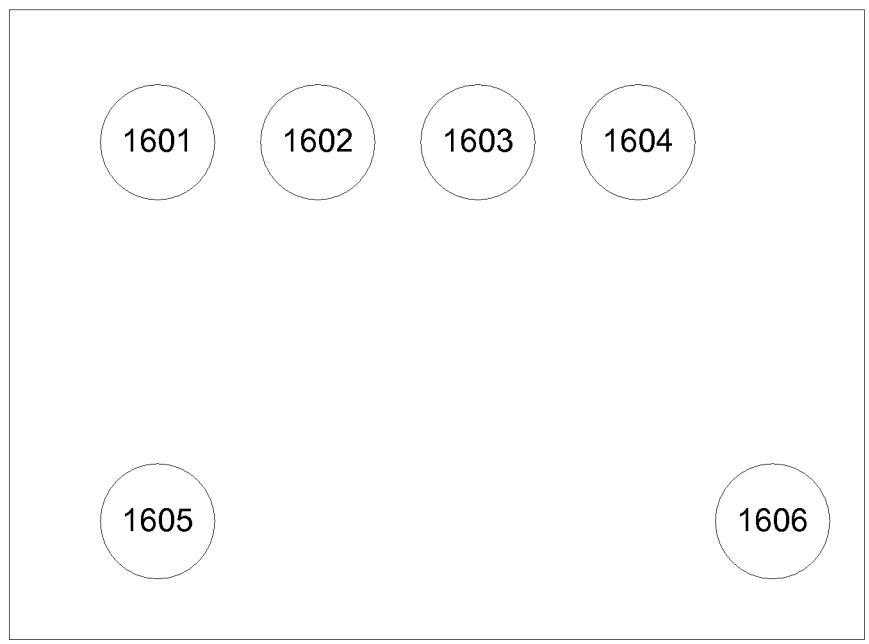
FIG. 2B shows another oximeter sensor unit opening pattern where one oximeter sensor unit opening is aligned asymmetrically with respect to the other oximeter sensor unit openings.

FIG. 2B shows a variation of the implementation of the oximeter sensor unit shown in FIG. 2B. The oximeter sensor unit in this specific implementation is also arranged to include six openings 1601-1606. Similar to FIG. 2A, openings 1601-1604 are arranged in a line closer to a first edge of the sensor, while openings 1605 and 1606 are arranged closer to a second edge, which is opposite the first edge. In one implementation, openings 1601-1604 are detector structures while openings 1605 and 1606 are source structures.

In this figure, the openings are positioned so that a line drawn through openings 1601-1604 is parallel to a line through openings 1605 and 1606. However, a line drawn through openings 1601 and 1605 is not parallel to a line through openings 1604 and 1606.

Additionally, similar to FIG. 2A, the distance between openings 1601 and 1604 is shorter than the distance between openings 1605 and 1606. Thus, the distance between openings 1601 and 1605 does not equal the distance between openings 1601 and 1606; the distance between openings 1602 and 1605 does not equal the distance between openings 1603 and 1605; and the distance between openings 1603 and 1605 does not equal the distance between openings 1604 and 1606.

In this implementation, the oximeter sensor unit itself is of a greater area relative to the area of the oximeter sensor unit shown in FIG. 2A. In another implementation, the oximeter sensor unit may be of a smaller area relative to the area shown in FIG. 2A. In yet another implementation, the oximeter sensor unit may be of a greater area relative to that shown in FIG. 2B.

Further, in a specific implementation, the openings are the same size as each other (e.g., each opening has the same diameter or each opening has the same area). A specific implementation uses one-millimeter circular openings. However, in another implementation, the diameter of one opening may be different from other openings, or there may be some openings with different diameters than other openings. There can be any combination of differently sized openings on one oximeter sensor unit. For example, there are two openings with a C size and other openings have a D size, where C and D are different and D is greater than C. Also, openings are not necessarily circular. So, C and D may represent area values.

Figure 2C:
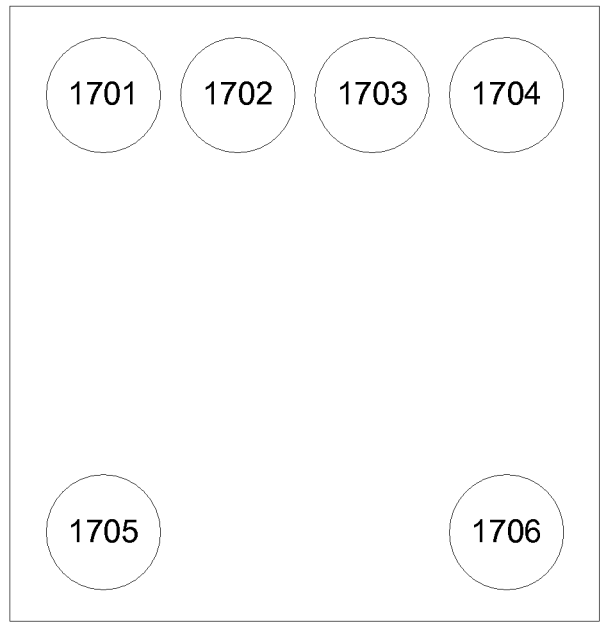
FIG. 2C shows an oximeter sensor unit opening pattern where the openings are arranged symmetrically about a vertical axis.

FIG. 2C shows another variation of the implementation of the oximeter sensor unit shown in FIG. 2A. The oximeter sensor unit in this specific implementation is also arranged to include six openings 1701-1706. Similar to FIGS. 2A and 2B, openings 1701-1704 are arranged in a line closer to a first edge of the sensor, while openings 1705 and 1706 are arranged closer to a second edge, which is opposite to the first edge. In one implementation, openings 1701-1704 are detector structures while openings 1705 and 1706 are source structures.

In this figure, the openings are positioned so that a line drawn through openings 1701-1704 is parallel to a line through openings 1705 and 1706. In fact, these two lines are equal in length. Furthermore, a line drawn through openings 1701 and 1705 is parallel (and equal in length) to a line through openings 1704 and 1706.

Thus, in this specific implementation, the distance between openings 1701 and 1706 is equal to the distance between openings 1704 and 1705. This specific arrangement includes further equalities: the distance between openings 1702 and 1705 equals that between openings 1703 and 1706 and the distance between openings 1703 and 1705 equals that between openings 1702 and 1706.

In an implementation, the distances between openings 1701-1704, 1704-1706, 1706-1705, and 1705-1701 are equal; thus, in this implementation openings 1701, 1704, 1706, and 1705 form the vertices of a square. In other implementations, however, four openings may form the vertices of any quadrilateral, such as a rectangle, a rhombus, a trapezoid, or a parallelogram.

Aside from the equalities mentioned, the distances between each of the openings 1701-1704 and each of the openings 1705-1706 are not equal. For instance, the distance between openings 1701 and 1705 does not equal the distance between openings 1701 and 1706.

Figure 2D:
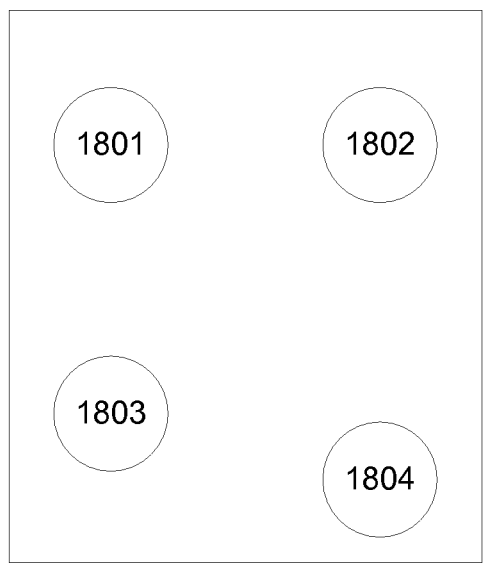
FIG. 2D shows another oximeter sensor unit opening pattern where one oximeter sensor unit opening is aligned asymmetrically with respect to the other oximeter sensor unit openings.

FIG. 2D shows a specific implementation of an oximeter sensor unit which is arranged to include four openings 1801-1804. Openings 1801 and 1802 are arranged in a line closer to a first edge of the sensor, while openings 1803 and 1804 are arranged closer to a second edge, which is opposite the first edge. In fact, opening 1804 is closer than opening 1803 to the second edge.

In one implementation, openings 1801 and 1802 are detector structures and openings 1803 and 1804 are source structures. However, in other implementations, there can be one or more detector structures, two or more detector structures, one or more source structures, or two or more source structures. For example, there may be three detector structures and one source structure or one detector structure and three source structures.

In FIG. 2D, the openings are positioned asymmetrically such that a line drawn through openings 1801 and 1802 is not parallel to a line through openings 1803 and 1804. However, a line drawn through openings 1801 and 1803 is parallel to a line through openings 1802 and 1804.

Additionally, the distance between openings 1801 and 1802 is shorter than the distance between openings 1803 and 1804. Thus, in FIG. 2D, the distance between openings 1801 and 1803 does not equal the distance between openings 1802 and 1804 and the distance between openings 1802 and 1803 does not equal that between openings 1802 and 1804.

Figure 2E:
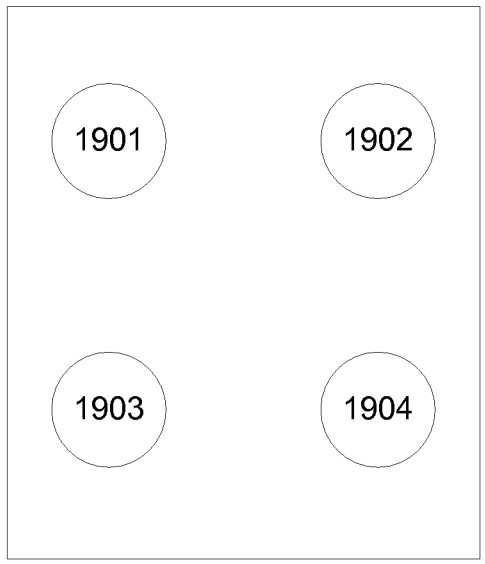
FIG. 2E shows an oximeter sensor unit opening pattern where the openings are arranged symmetrically about horizontal and vertical axes.

FIG. 2E shows a variation of the implementation of the oximeter sensor unit shown in FIG. 2D. The oximeter sensor unit of this implementation also includes four openings 1901-1904. Openings 1901 and 1902 are arranged in a line closer to a first edge of the oximeter sensor unit, while openings 1903 and 1904 are arranged closer to a second edge, which is opposite the first edge. In one implementation, openings 1901 and 1902 are detector structures and openings 1903 and 1904 are source structures.

In FIG. 2E, the openings are positioned symmetrically such that a line drawn through openings 1901 and 1902 is parallel, and equal, to a line through openings 1903 and 1904. Additionally, a line drawn through openings 1901 and 1903 is parallel, and equal, to a line through openings 1902 and 1904.

In an implementation, the distances between openings 1901-1902, 1902-1904, 1904-1903, and 1903-1901 are equal; thus, in this implementation openings 1901, 1902, 1903, and 1904 form the vertices of a square. In other implementations, however, four openings may form the vertices of any quadrilateral, such as a rectangle, a rhombus, a trapezoid, or a parallelogram.

Some of the distances between the centers of particular openings are unequal; for instance, the distance between openings 1901 and 1903 does not equal the distance between openings 1901 and 1904.

Figure 2F:
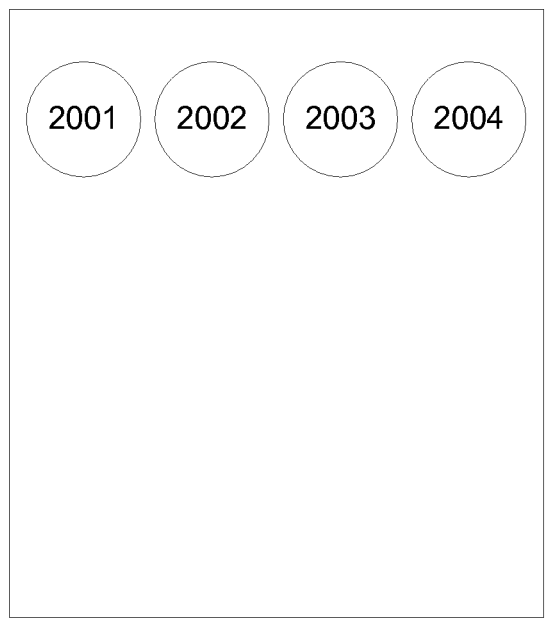
FIG. 2F shows an oximeter sensor unit opening pattern where the openings are aligned in a row.

FIG. 2F shows another variation of the implementation of the oximeter sensor unit shown in FIG. 2D. Similar to FIGS. 2D and 2E, this specific implementation of an oximeter sensor unit includes four openings 2001-2004.

However, in this variation, four of the openings are arranged in a line closer to a first edge of the sensor. Specifically, in this figure, openings 2001-2004 lie in a row parallel to the first edge so that a straight line may be drawn through each opening. In one implementation, openings 2001 and 2002 are detector structures and openings 2003 and 2004 are source structures.

In this specific implementation, the distance between openings 2001 and 2002 is equal to the distance between openings 2002 and 2003; this distance is also equal to that between openings 2003 and 2004.

Additionally, the distance between openings 2001 and 2003 equals that between openings 2002 and 2004. In fact, this distance is twice the distance between each individual opening. Thus, the distance between openings 2001 and 2003 does not equal that between openings 2001 and 2002; the former is twice the distance of the latter.

Figure 2G:
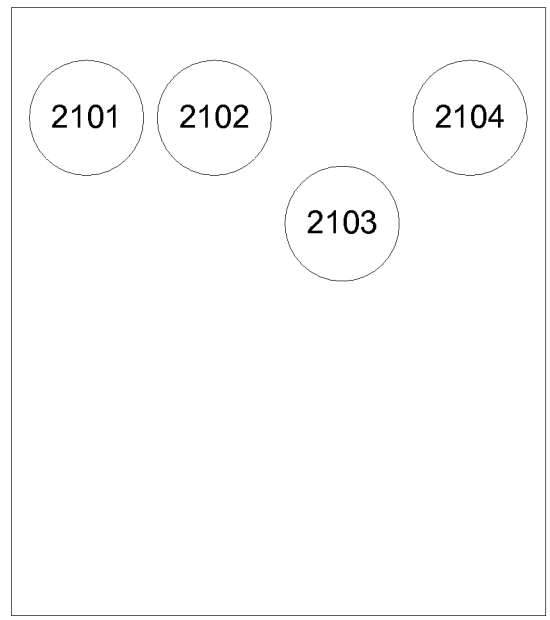
FIG. 2G shows an oximeter sensor unit opening pattern where the openings are aligned in a row, except for one of the openings.
Figure 2H:
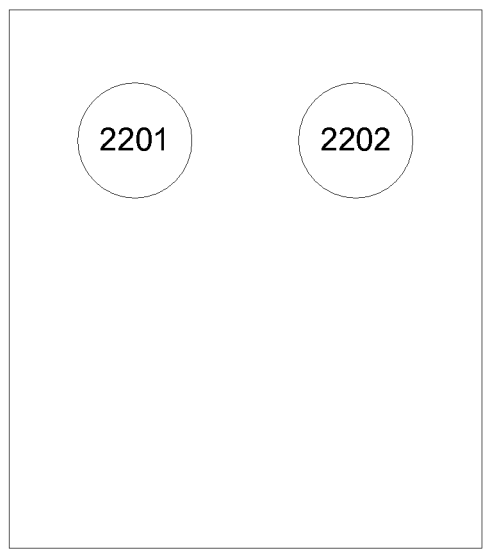
FIG. 2H shows an oximeter sensor unit opening pattern with two openings.

FIG. 2G shows a variation of the implementation of the oximeter sensor unit shown in FIG. 2H. This implementation of an oximeter sensor unit is similarly arranged to include four openings 2101-2104. Also, this arrangement of openings is located closer to a first edge of the sensor. However, in this figure, openings 2101, 2102, and 2104 lie in a row parallel to the first edge so that a straight line may be drawn through the center of each opening, while opening 2103 lies below that straight line.

In this implementation, opening 2103 lies equally spaced between openings 2102 and 2104; in other implementations, opening 2103 can lie closer to one opening than another. In one implementation, openings 2101 and 2102 are detector structures and openings 2103 and 2104 are source structures.

In this specific implementation, as mentioned above, the distance between openings 2102 and 2103 equals that between openings 2103 and 2104. Aside from this equality, the distances between the openings are unequal. For example, in this implementation, the distance between openings 2101 and 2103 does not equal the distance between openings 2102 and 2104, and the distance between openings 2102 and 2103 does not equal that between openings 2102 and 2104.

FIG. 2H shows a specific implementation of an oximeter sensor unit which is arranged to include two openings 2201 and 2202. Similar to FIGS. 2F and 2G, this arrangement of openings is located closer to a first edge of the oximeter sensor unit. Additionally, openings 2201 and 2202 lie in a row parallel to the first edge so that a straight line may be drawn through each opening. In one implementation, opening 2201 is a detector structure and opening 2202 is a source structure.

Although we have shown oximeter sensor units with two, four, and six openings in these figures, other implementations may include different numbers of oximeter sensor unit openings. For instance, there may be three, five, seven, eight, or more openings.

Further, there may be any combination of detector structures and source structures and the number of detector structures need not equal the number of source structures. For instance, if there are three openings, there may be one detector structure and two source structures or two detector structures and one source structure. As another example, if there are eight openings, there may be two detector structures and six source structures, five detector structures and three source structures, or four detector structures and four source structures.

The distance between one opening to another (e.g., between a source structure and a detector structure) in an oximeter sensor unit can also vary depending on many factors including the nature and the depth of a tissue to be examined. In one embodiment, a source structure and a detector structure may be separated by about 20 millimeters. In another embodiment, a source structure and a detector structure may be separated by about 10 millimeters. In another embodiment, a source structure and a detector structure may be separated by about 5 millimeters. In yet another embodiment, a source structure and a detector structure may be separated by 2 millimeters. Many other variations of opening distances can be implemented in embodiments of the present invention.

III. Tissue Contact and Pressure Sensors

In some embodiments of the invention, a sensor panel can include a feature that allows the sensor panel to be closely attached to a tissue without constricting a blood flow in the tissue. It is desirable to include such a feature, because good contact between the tissue and the sensor panel can result in a more accurate oxygenation reading of the tissue.

One example of such a feature is an adhesive. A sensor panel can include an adhesive on the surface of the sensor panel that will contact a tissue. The sensor panel can further include a release layer, protecting the adhesive until the sensor panel is applied to the tissue. An adhesive has suitable peel strength so that the sensor panel can be securely attached to the skin, but can be peeled off readily without causing much discomfort to a patient. Such skin-friendly adhesives are well-known in the art and can be incorporated in embodiments of the invention.

In some clinical situations, it may be impractical to include an attachment feature such as an adhesive on a sensor panel. For example, when a patient has certain skin conditions (e.g., decubitus ulcers, eczema, or psoriasis), it is not desirable to use an adhesive to attach a sensor panel to the patient's skin. The use of an adhesive may further aggravate the patient's skin condition that is already compromised. In these and other situations, it may be desirable to include another feature in the sensor panel which can indicate whether or not there is good contact between the sensor panel and a tissue.

Figure 3:
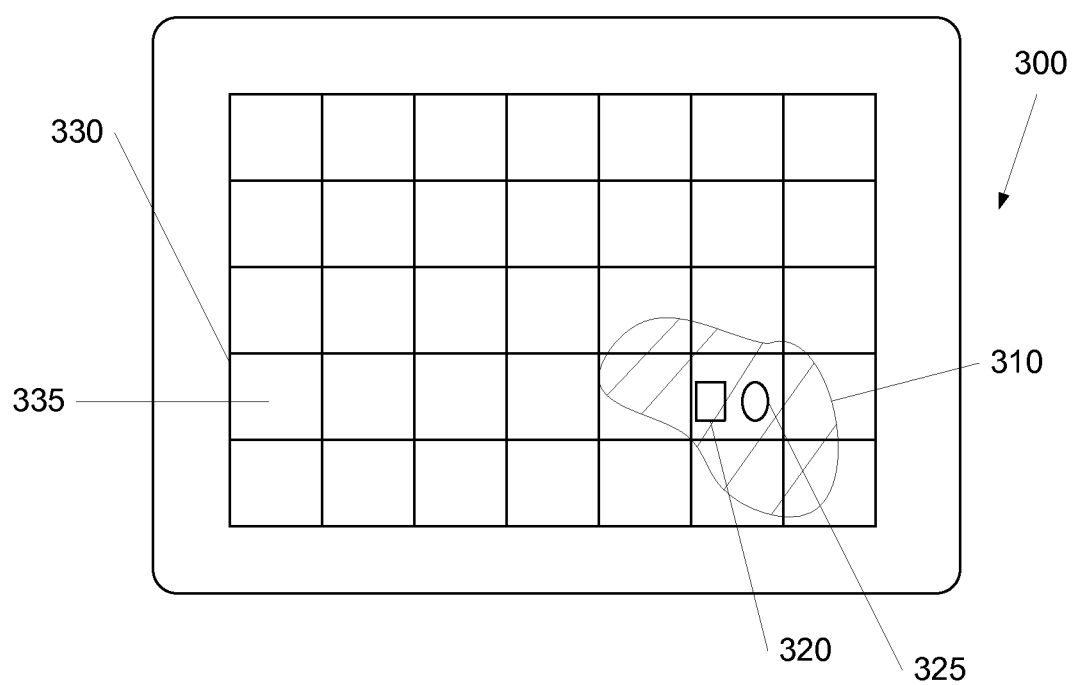
FIG. 3 shows a sensor panel including a flexible substrate including oximeter sensor units and pressure sensors connected to the flexible substrate.

In one embodiment of the invention, a sensor panel has pressure sensors integrated in or connected to a flexible substrate (in addition to oximeter sensor units) to determine whether or not there is good contact between the sensor panel and a tissue. FIG. 3 illustrates such an example. In this example, a sensor panel 300 includes oximeter sensor units 320 and pressure sensors 325 connected to or integrated into a flexible substrate 310. The oximeter sensor units and the pressure sensors are arranged in a form of a matrix 330 in the sensor panel 300. In each pixel element 335 in the matrix 330, a pressure sensor and an oximeter sensor unit are proximate to each other, occupying the same pixel element. While FIG. 3 shows that the pressure sensor and the oximeter sensor unit are next to each other in each pixel element, they may be placed on top of each other in the flexible substrate. Therefore, for each pixel element (i.e., a position in the sensor panel), one can read both pressure applied by the tissue to the sensor panel, as well as the oxygen saturation of the tissue contacting the pixel element.

If a pressure reading from a pixel element, e.g., pixel element 335, indicates that there is not good contact between a tissue and a sensor panel (e.g., 0 kilogram), then the oxygen saturation reading from the pixel element 335 may not be accurate and can be ignored. By contrast, if a pressure reading from the pixel element 335 meets a certain threshold (e.g., above 1 kilogram), indicating that there is proper contact between the tissue and the sensor panel, then the oxygen saturation reading from the pixel element 335 is accurate and should be recorded. The pressure reading from the pressure sensors can be an absolute measure or a relative measure of pressure applied to the sensor panel.

In one embodiment of the invention, pressure sensors can be a discrete set of pressure sensors. For example, a discrete set of pressure sensors (e.g., buttons that can be depressed) can be positioned proximate to each of oximeter sensor units, and both pressure sensors and oximeter sensor units can be connected to a flexible substrate. Various types of pressure sensors are can be implemented in embodiments of the invention. For example, miniature load cells can be connected to a flexible substrate and can measure pressure applied by a tissue onto a sensor panel at discrete points. Each pressure sensor and each oximeter sensor unit located at the same or proximate position (i.e., in the same pixel element) in the sensor panel can be electrically connected so that positional values of the sensor panel are generated together with pressure measurements and oxygen saturation measurements.

In another embodiment of the invention, pressure sensors can be a laminate of electroactive multilayered fabric. For example, a laminate of five fabric layers can be arranged to form a resistive touchpad. In the laminate, the outer and central layers are conductive, with two insulating layers around the central layer. The pressure sensor is contact activated when the layers are compressed together to form an electronic circuit. In other words, the laminate measures the voltage drop at various points on the surfaces to determine where and how hard the pressure was applied to the fabric. This type of electroactive multilayered fabrics is commercially available (e.g., ElekTex® sold by Eleksen Ltd.), and can be used in embodiments of the invention.

When an electroactive multilayered fabric is used as pressure sensors, a piece of an electroactive fabric can be attached (e.g., via stitching) to a flexible substrate in a sensor panel. Alternatively, the electroactive fabric can be used as a flexible substrate in a sensor panel and can be used to couple oximeter sensor units. The oximeter sensor units are electrically connected to the electroactive multilayer fabric so that positional values of the sensor panel are generated together with pressure measurements and oxygen saturation measurements.

IV. Sensor Panel Shape and Size, Linking Members and Sensor Panel Array

As shown in FIGS. 1A through 1D, a sensor panel can have any suitable shape and size. For example, a sensor panel can have a shape of a rectangle, square, triangle, circle, oval, and others. In one embodiment of the invention, a sensor panel can be rectangular in shape and has a side length of between about 2 to 30 centimeters, between about 4 to 20 centimeters, or between about 5 to 10 centimeters. For example, a sensor panel can be a rectangular panel, like the sensor panel shown in FIG. 1A, having a dimension of about 7 by 9 centimeters.

In some applications, it may be desirable to use a sensor panel having a much larger dimension. For example, if a doctor wishes to measure oxygen saturation of an immobile patient's body surface that is in contact with a bed, it may be desirable to use a sensor panel that can measure oxygen saturation of the entire body surface. While a single sensor panel can be produced in a large size, it may be easier to manufacture a sensor panel in a manageable size and then to use multiple sensor panels in conjunction. This way, sensor panels can be produced in a limited number of sizes and shapes and can be used to scan tissues of varying size and shape.

Figure 4:
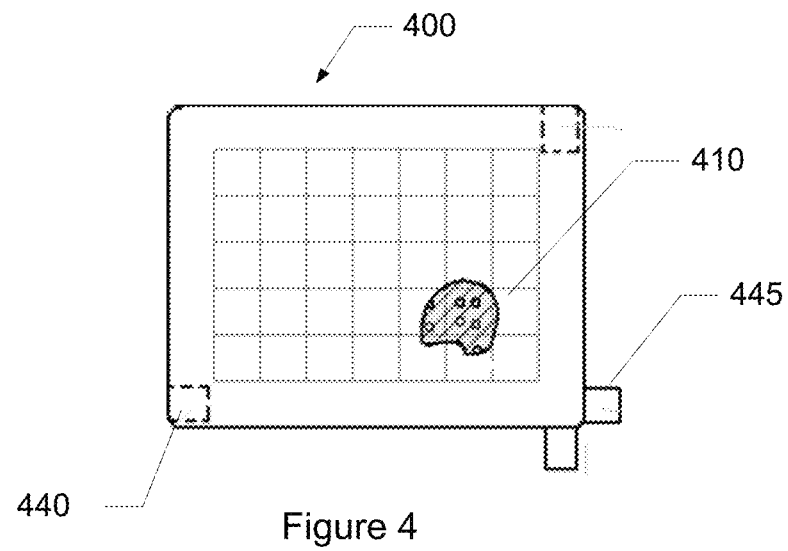
FIG. 4 shows a sensor panel further including linking members at or near a perimeter of the flexible substrate.

FIG. 4 illustrates an example of a sensor panel that can be joined to another sensor panel to form a much larger scanning surface. In FIG. 4, a sensor panel 400 has linking members 440 and 445 that are located at a perimeter of a flexible substrate 410. In some embodiments, each linking member is identical in structure and composition to another linking member of the sensor panel. In other embodiments, each linking member is different in structure and composition to another linking member of the sensor panel. The linking members shown in FIG. 4 are a set of male and female connectors. For example, the linking member 440 is a female connector, and the linking member 445 is a male connector. Examples of female and male connectors include snap buttons, Velcro® hook and loop fasteners, and others.

Figure 5:
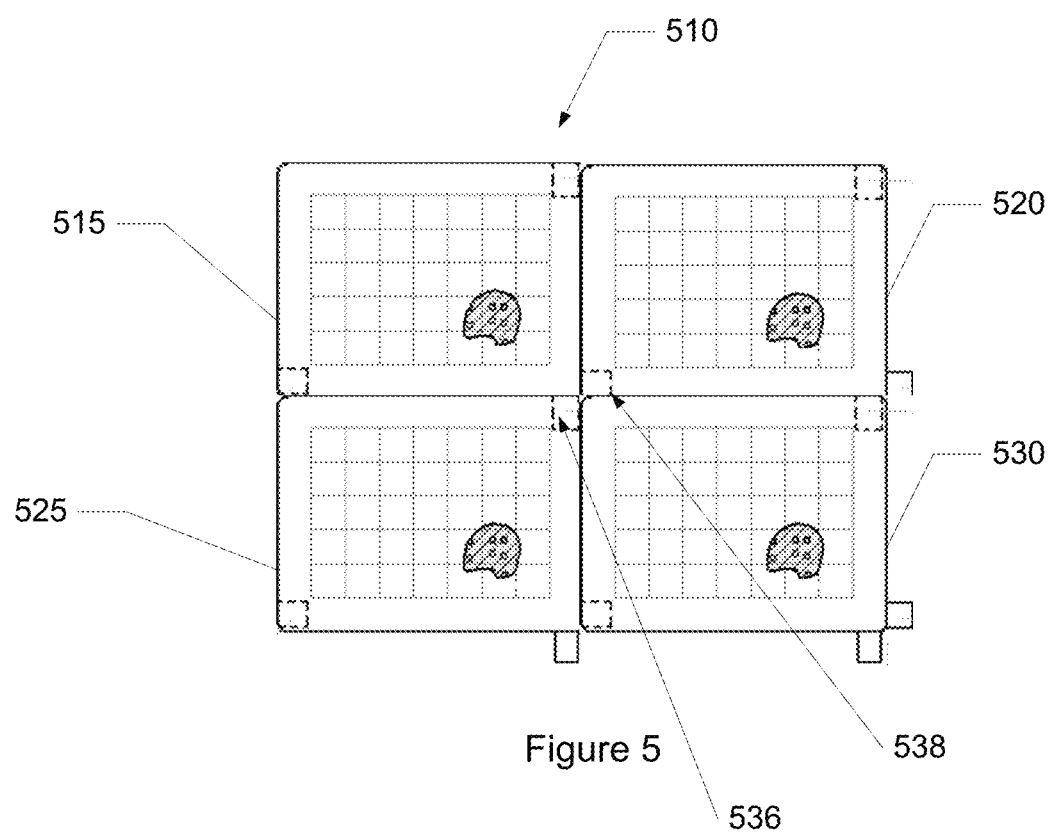
FIG. 5 shows a sensor panel array including four rectangular sensor panels tiled together by linking members.

FIG. 5 shows an example of how linking members can be used together to produce a sensor panel array including two or more sensor panels tiled together. Shown in FIG. 5 are four sensor panels 515, 520, 525, and 530 that are joined together using their respective linking members. Region 538 is an area that joins the panel 515 and the panel 520 using a male linking member of the panel 515 and a female linking member of the panel 520. Region 536 is an area that joins the panel 515 and the panel 525 using a male linking member of the panel 515 and a female linking member of the panel 525. While FIG. 5 shows four sensor panels tiled together to produce a sensor panel array, any number of sensor panels can be tiled together to produce a sensor panel array of a desired size. Also, while FIG. 5 shows four identical sensor panels joined together, a sensor panel array can be put together by joining sensor panels having different properties (e.g., varying shapes or arrangements of oximeter sensor units).

Although FIGS. 4 and 5 illustrate a sensor panel having linking members extending beyond the perimeter of the flexible substrate, the linking members can be located at other suitable locations of the sensor panel. In one embodiment, linking members can be located inside of the perimeter of the flexible substrate. For example, hook fasteners of a Velcro® can be attached inside of two edges of the flexible substrate, and loop fasteners of a Velcro® can be attached inside of the other two edges of the flexible substrate. When such linking members are used, the edges of the sensor panels may overlap when the sensor panels are tiled together to produce a sensor panel array.

In another embodiment, linking members can be a structural part of the perimeter of a sensor panel. For example, a sensor panel can have a perimeter that has a puzzle-cut shape with finger-like projections. When such sensor panels are assembled together, puzzle-cut seams can form between the sensor panels, producing a sensor panel array.

While linking members of a sensor panel can be used to join multiple sensor panels together physically, they can also be used to functionally connect one sensor panel to another. For example, the linking members may include electrical wires or optical wires to send electrical or optical signals from one sensor panel to another. In some embodiments, one or more linking members of a sensor panel can be used to couple the sensor panel to other system components. For example, a linking member can be a female or male end of a plug for a cable that connects electrical wires and/or optical fibers of the sensor panel to other system components, such as a control unit. A control unit can send a signal to a sensor panel through linking members so that a sensor panel can emit light onto a tissue or detect light reflected from the tissue.

In another example, a linking member can include an electrical connection to a display monitor or to a speaker to assist a user to monitor oxygen saturation of a tissue. In another example, a linking member can include a connection to a display monitor, or a speaker. In another example, the linking member can include a cable that allows a sensor panel to be connected to a power source, such a battery. Thus, linking members of a sensor panel can be used both physically and functionally to connect one sensor panel to other sensor panels or to other system components.

A sensor panel or a sensor panel array described above can be incorporated as a part of another structure. For example, a sensor panel or a sensor panel array can be incorporated into a bed sheet, or a garment such as sock, glove, headband, hat, and others. If a patient has a poor circulation in his leg and is at risk of developing gangrene, a sensor panel can be incorporated into a sock so that oxygenation of the patient's leg can be monitored. If a patient who is on a prolonged bed rest is at risk of developing pressure ulcers, then one or more sensor panels can be incorporated into a bed sheet to monitor the patient. Since embodiments of the invention are flexible, they can be incorporated into unlimited types of garments and fabric products.

V. System

Figure 6:
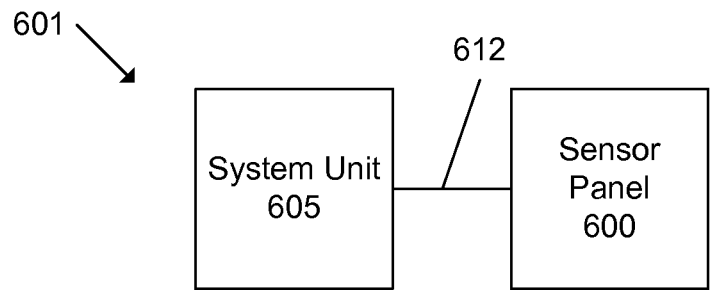
FIG. 6 shows a system for measuring oxygen saturation of a tissue, where the system includes a sensor panel and a system unit.

One or more features described above can be incorporated into a system so that oxygen saturation level of a tissue can be measured and analyzed. FIG. 6 shows an example of such a system. A sensor system 601 contains a system unit 605 and a sensor panel 600, which is connected to the system unit via a wired connection 612. As described above, the sensor panel 600 can comprise a flexible substrate and oximeter sensor units connected to the flexible substrate. In some embodiments, the sensor panel can further comprise pressure sensors. Connection 612 may be an electrical, optical, or another wired connection including any number of wires (e.g., one, two, three, four, five, six, or more wires or optical fibers), or any combination of these or other types of connections. In other implementations of the invention, however, connection 612 may be wireless such as via a radio frequency (RF) or infrared communication.

Typically, the system is used by placing the sensor panel in contact or close proximity to tissue (e.g., skin) at a site where an oxygen saturation, pressure, or other related measurement is desired. The system unit causes an input signal to be emitted by source structures in the sensor panel into the tissue (e.g., human tissue). There may be multiple input signals, and these signals may have varying or different wavelengths. The input signal is transmitted into or through the tissue.

Then, after transmission through or reflection off the tissue, the signal is received by detector structures in the sensor panel. This received signal is received and analyzed by the system unit. Based on the received signal, the system unit determines the oxygen saturation of the tissue and provides an output signal (e.g., a visual or audible signal).

In an implementation, the system is a tissue oximeter, which can measure oxygen saturation without requiring a pulse or heart beat. A tissue oximeter of the invention is applicable to many areas of medicine and surgery including plastic surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference along with all other references cited in this application.

Various equations for self-calibration schemes are also known in the art. Self-calibration schemes are used to adjust for system factors such as source intensity, detector gain, and loss of light in the optical fibers and connectors. The self-calibration scheme may include equations discussed in U.S. Pat. Nos. 6,516,209, 6,735,458, and 6,078,833, and *New Optical Probe Designs for Absolute (Self-Calibrating) NIR Tissue Hemoglobin Measurements, Proc.* SPIE 3597, pages 618-631 (1999), which are incorporated by reference. The attenuation ratio method may also include techniques discussed in U.S. Pat. No. 6,587,701, which is incorporated by reference.

Figure 7A:
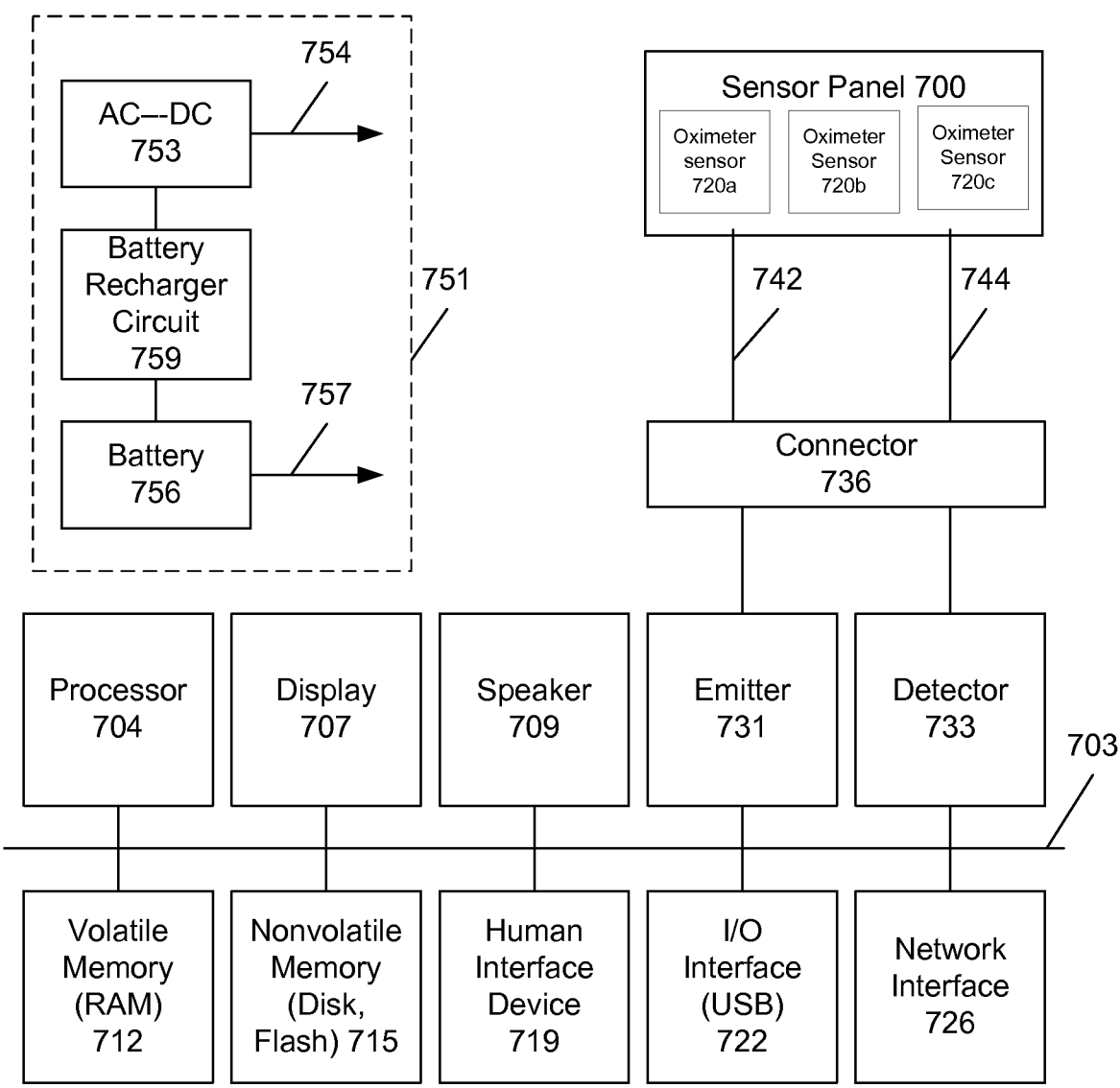
FIG. 7A shows detail of a specific implementation of the system of FIG. 6.

FIG. 7A shows a specific implementation of the system of FIG. 6, where some of the components of the system are shown in greater detail. The system unit includes a processor 704, display 707, speaker 709, emitter 731, detector 733, volatile memory 712, nonvolatile memory 715, human interface device or HID 719, I/O interface 722 (e.g., USB), and network interface 726. These components can be housed within a single system unit enclosure or separately The components are linked together using a bus 703, which represents the system bus architecture of the system. Although this figure shows one bus that connects to each component, the busing is illustrative of any interconnection scheme serving to link the subsystems. For example, speaker 709 could be connected to the other subsystems through a port or have an internal direct connection to processor 704.

A sensor panel 700 has oximeter sensor units 720a, 720b, and 720c. While three oximeter sensor units are shown as an example, the sensor panel can have fewer or more oximeter sensor units. The sensor panel 700 is then connected to the system unit components by a connector 736. The connector 736 connects the sensor panel 700 using one or more wires 742 and 744. The connector removably connects the sensor panel and its wires to the emitter and detectors in the system unit. There is one cable or set of cables 742 to connect to the emitter, and one cable or set of cables 744 to connect to the detector. In an implementation the cables are fiber optic cables, but in other implementations, the cables are electrical wires.

Emitter 731 is a light source that emits light at one or more specific wavelengths. In a specific implementation, two wavelengths of light (e.g., 690 nanometers and 830 nanometers) are used. In other implementations, other wavelengths of light may be used. Detector 733 is typically a photodetector capable of detecting the light at the wavelengths produced by the emitter.

The connector may have a locking feature; e.g., insert connector, and then twist or screw to lock. If so, the connector is more securely held to the system unit and it will need to be unlocked before it can be removed. This will help prevent accidental removal of the sensor panel or sensor panel array.

The connector may also have a first keying feature, so that the connector can only be inserted into a connector receptacle of the system unit in one or more specific orientations. This will ensure that proper connections are made.

The connector may also have a second keying feature that provides an indication to the system unit which type of sensor panel is attached. The system unit may handle making measurements for a number of different types of sensor panels. When a sensor panel is inserted, the system uses the second keying feature to determine which type of sensor panel is connected to the system. Then the system can perform the appropriate functions, use the proper algorithms, or otherwise make adjustments in its operation for the specific type of sensor panel.

For example, when the system detects that a rectangular sensor panel as shown in FIG. 1A is connected, the system uses proper algorithms and operation for that sensor panel. When the system detects a square sensor panel shown in FIG. 1C, the system uses proper algorithms and operation for that sensor panel. A system can handle any number of different types of sensor panels. There may be different sensor panels for measuring different parts of the body, or different sizes or versions of a sensor panel measuring a part of the body.

With the second keying feature, the system will be able to distinguish between the different sensor panels. The second keying feature can use any type of coding system to represent each sensor panel including binary coding. For example, for a sensor panel, there are four second keying inputs, each of which can be a logic 0 or 1. With four second keying inputs, the system will be able to distinguish between sixteen different sensor panels.

In various implementations, the system is powered using a wall outlet or battery powered, or both. Block 751 shows a power block of the system having both AC and battery power options. In an implementation, the system includes an AC-DC converter 753. The converter takes AC power from a wall socket, converts AC power to DC power, and the DC output is connected to the components of the system needing power (indicated by an arrow 754). In an implementation, the system is battery operated. The DC output of a battery 756 is connected to the components of the system needing power (indicated by an arrow 757). The battery is recharged using a recharger circuit 759, which received DC power from an AC-DC converter. The AC-DC converter and recharger circuit may be combined into a single circuit.

The processor 709 may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor panels at different locations.

A computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, and volatile media. The invention may be embodied in a computer program product.

The nonvolatile memory 715 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The volatile memory 712 includes static or dynamic memory, such as cache memory or RAM.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Computer software products may be written in any of various suitable programming languages, such as C, C++, C #, Pascal, Fortran, Perl, Matlab (from MathWorks, www-.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Other operating systems may be used, including custom and proprietary operating systems.

Furthermore, the system may be connected to a network and may interface to other systems using this network. The network interface 726 may be an intranet, internet, or the Internet, among others. The network may be a wired network, a wireless network, telephone network, packet network, an optical network (e.g., using optical fiber), or any combination of these. For example, data and other information may be passed between the computer and components (or steps) of a system of the invention using a wireless network using a protocol such as Wi-Fi. For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

The components shown in FIG. 7A can be added, deleted, and combined. Also, the system may also include other components not shown.

VI. Sensor Panel and Multiplexer

Figure 7B:
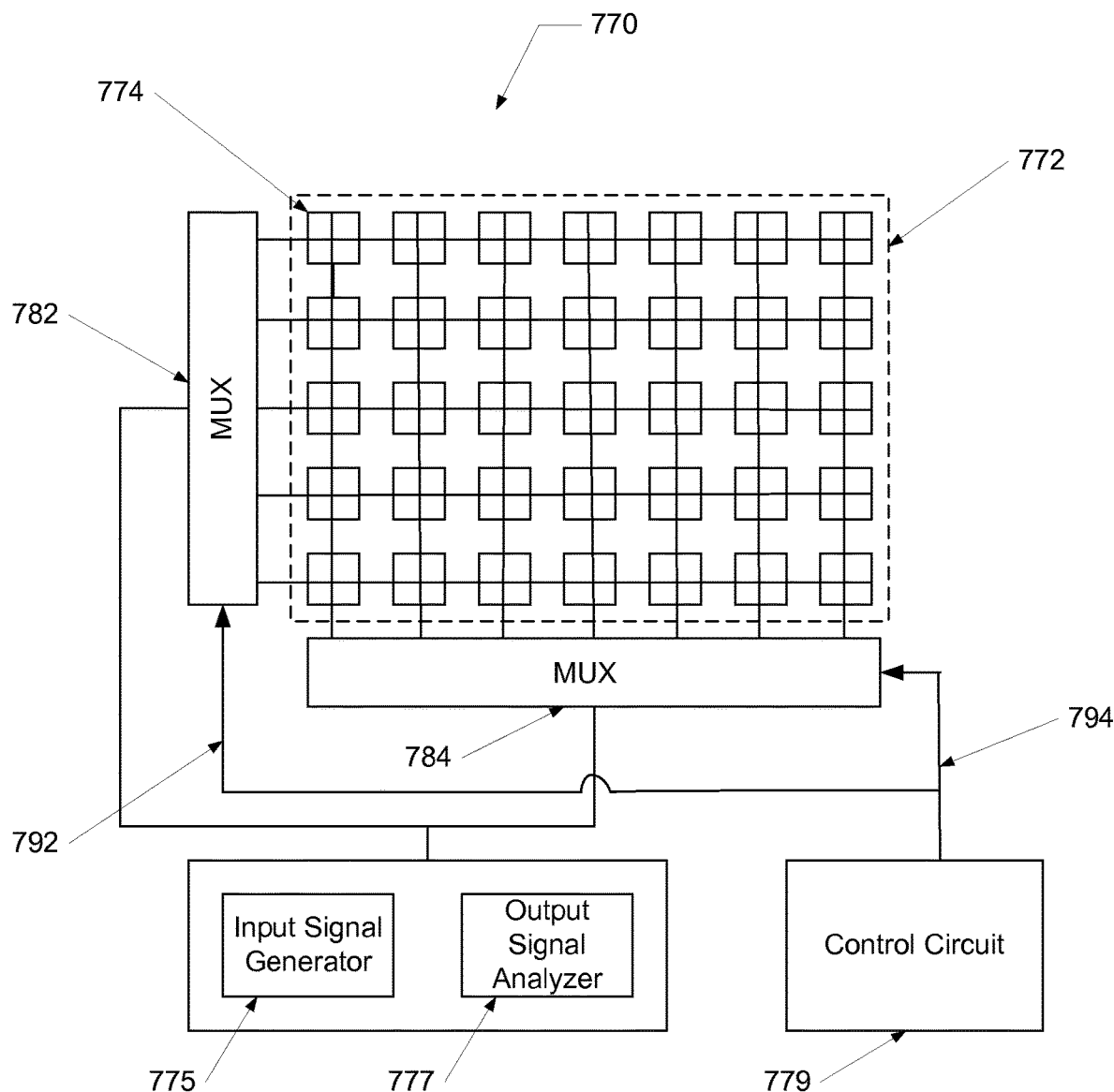
FIG. 7B shows how multiplexers are used to address each oximeter sensor unit in a sensor panel.

FIG. 7B is a schematic diagram of a specific implementation of the invention shown in FIG. 6. This figure illustrates how measurements can be made from each oximeter sensor unit in a sensor panel. The system 770 has a sensor panel 772 including oximeter sensor units 774, an input signal generator 775, and an output signal analyzer 777.

An input signal generated by the input signal generator 775 is connected to the sensor panel 772 by a row multiplexer 782. An output signal generated by the sensor panel 772 is connected to the output signal analyzer 777 by a column multiplexer 784. In an embodiment where a sensor panel has LEDs and photodiodes as source structures and detector structures, respectively, the input signal and the output signal are electrical signals. In another embodiment where a sensor panel has optic fibers as part of source structures and detector structures, the input signal and the output signal are optical signals.

As shown in FIG. 7B, the oximeter sensor units in the same row are connected to multiplexer 782 through a single connector line (e.g., conductors), shown as a horizontal line across the row of the oximeter sensor units. The oximeter sensor units in the same column are connected to multiplexer 784 through another connector line, shown as a vertical line across the column of the oximeter sensor units.

A control circuit 779 controls switching of multiplexers 782 and 784 through control lines 792 and 794 so that each specific oximeter sensor unit in the array can be addressed. For example, scanning the entire matrix may be accomplished by addressing each sensor unit row by row, or column by column. Scanning may be performed repeatedly as desired.

A specific location in the matrix may be directly addressed. For example, control circuit 779 sends a signal to multiplexer 782 to connect to the top row (i.e., row 1) of oximeter sensor units and multiplexer 784 to connect to the leftmost column (i.e., column 1). Then, the sensor unit at row 1, column 1 will be specifically addressed, and signals to and from the generator and analyzer will be directed to and from that sensor unit. Any sensor unit in the array may be similarly accessed.

VII. Sensor Panel and Output

Figure 8:
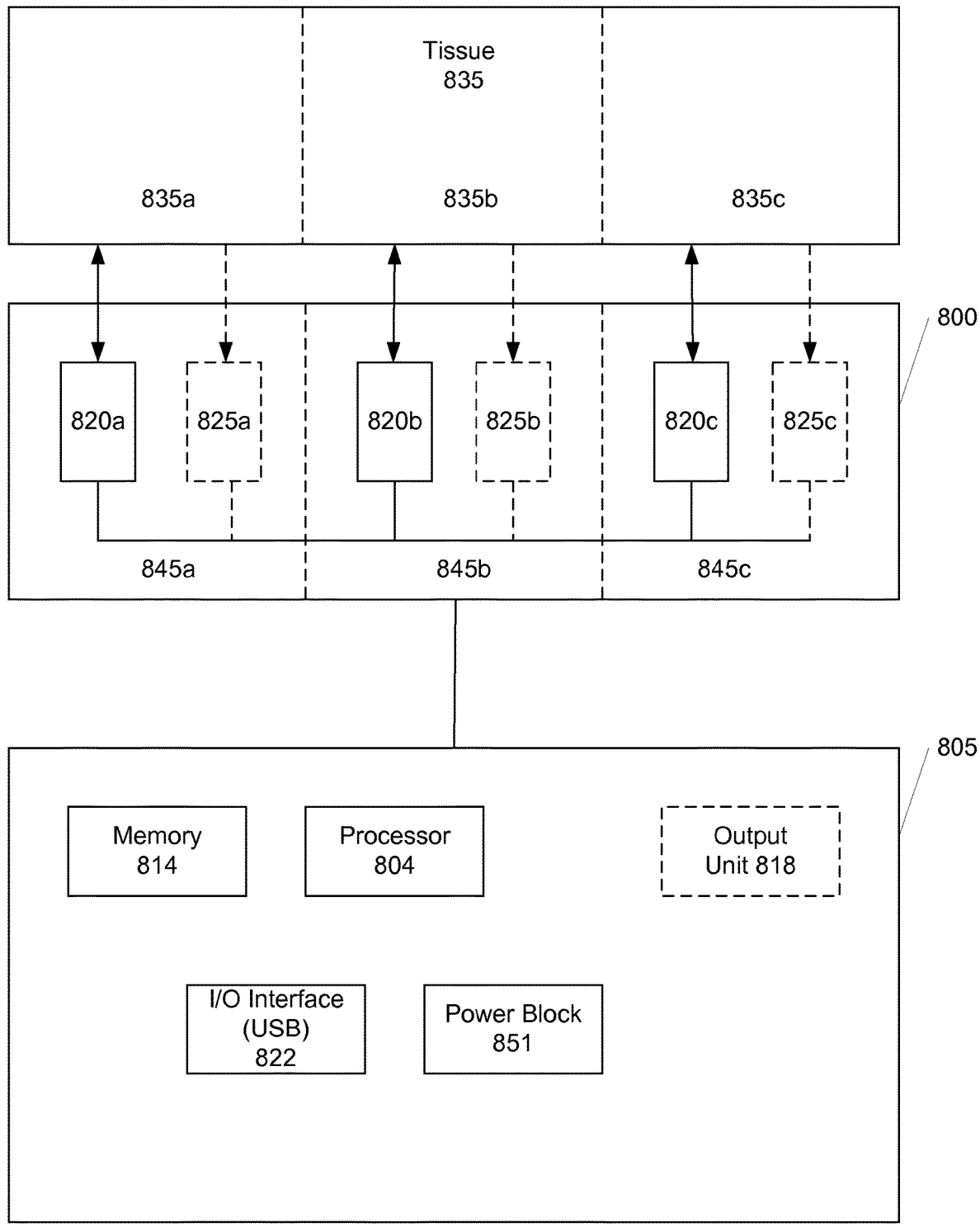
FIG. 8 shows a block diagram of a specific implementation of the system of FIG. 6, showing the arrangement of oximeter sensor units and pressure sensors in a sensor panel.

FIG. 8 shows a block diagram of a specific implementation of a system of the invention shown in FIG. 6. This implementation includes a system unit 805 and a sensor panel 800. Typically, the sensor panel 800 is connected the system unit 805 through a connector as described above in FIG. 6.

FIG. 8 shows a system unit 805 that governs operation of the system. Details of some of the components of the system unit are analogous to those shown in FIG. 7 and may be discussed above. For example, memory 814 can be either volatile memory 712 or nonvolatile memory 715, or both shown in FIG. 7. Power block 851 is analogous to power block 751 shown in FIG. 7, and it may comprise one or more components of the power block 751 shown in FIG. 7. Input/Output Interface 822 is analogous to Input/Output Interface 722 shown in FIG. 7, and it can be an USB interface. Processor 804 is analogous to processor 704, and it analyzes, among other things, measured oxygen saturation and pressure. An output unit 818 can be a display 707 or a speaker 709, or other types of output not shown in FIG. 7.

In one implementation of the invention, the system unit 805 is a large, nonportable device that is attached to a wall or secured to a stand or surface. In this implementation, the system is typically connected to AC power. A battery may be used as a back-up the AC power.

In another implementation of the invention, the system unit 805 is a portable console. It is desired that it is a light console that can be hand-carried by a user. A portable console can follow a patient and oxygen saturation measurements can be made anywhere in the hospital. It is desirable that the portable console is battery-operated. The battery can be a rechargeable type, such as nickel cadmium (NiCd), nickel metal hydride (NiMH), and lithium ion (Li-Ion) rechargeable batteries.

In yet another implementation of the invention, the system unit 805 can be integrated into a flexible substrate of a sensor panel or a sensor panel array. In this implementation, the system unit should be very compact and can be, for example, a single chip system processor with all comprehensive drive elements, powered by a small battery. It is desired that an output unit in this embodiment is simple and compact, such as an alarm which can alert a user when certain measurements fall below a threshold. In this embodiment, the entire system can be integrated into a flexible product (e.g., a bed sheet or a garment), and this product can function on its own without any outside sources to run the system.

To measure oxygen saturation, the sensor panel 800 is placed on a tissue 835 where the measured oxygen saturation is desired. Light from the sensor panel 800 is transmitted and scattered into the tissue, and some light is reflected back to the sensor panel. Based on the transmitted and received light, the system unit 805 calculates oxygen saturation of the tissue.

The sensor panel 800 includes sensor unit 820*a*, 820*b*, and 820*c* located at pixel elements 845*a*, 845*b*, and 845*c*, respectively, of the sensor panel 800. While only three oximeter sensor units are shown in the sensor panel 800, any suitable number of oximeter sensor units can be included in the sensor panel. Each of the oximeter sensor units in the sensor panel measures an oxygen saturation value of a tissue area or region that approximately corresponds to the location of each oximeter sensor unit. For example, the oximeter sensor unit 820*a* measures an oxygen saturation value of a tissue area 835*a*. The oximeter sensor unit 820*b* measures an oxygen saturation value of a tissue area 835*b*. The oximeter sensor unit 820*c* measures an oxygen saturation value of a tissue area 835*c*. While dotted lines are drawn among different tissue areas 835*a*, 835*b*, and 835*c* as an illustration, each oximeter in the sensor panel may also detect light scattered from other tissue areas.

In FIG. 8, an emitter and a detector are not shown. As described above, in one embodiment of the invention, emitters and detectors are located in the sensor panel. For example, the emitters are source structures (e.g., LEDs) positioned in the oximeter sensor units and detectors are detector structures (e.g., photodiodes) positioned in the oximeter sensor units. In this embodiment, the oximeter sensor units in the sensor panel can be connected to the system unit 805 by a cable containing electrical wires so that LEDs and photodiodes can be powered from the system unit.

In another embodiment, an emitter and a detector are located outside of the sensor panel, e.g., in the system unit 805. In this embodiment, a source structure is an opening in an oximeter sensor unit (at its scanning surface) with an optical fiber inside, and a detector structure is an opening in the oximeter sensor unit with an optical fiber inside. In this embodiment, the optical fibers from the source structure and the detector structure are connected to the emitter and the detector, respectively, which may be located in the system unit 805. Light generated by the emitter in the system unit is transmitted to the source structures in the oximeter sensor units, which is subsequently transmitted to the tissue. Light transmitted and reflected from the tissue is collected by the detector structures in the oximeter sensor units and is transmitted to the detector in the system unit via fiber optic cables.

Regardless of the locations of emitter(s) and detector(s), an emitter typically emits light in the visible or infrared range and can emit light of one or more specific wavelengths. Human tissues include deoxygenated and oxygenated hemoglobins which are the most dominant chromophores in the spectrum range of 600 nanometers to 900 nanometers. Light-absorption and light-scattering patterns differ significantly among these two forms of hemoglobins at certain wavelengths of light. In a specific implementation, two wavelengths of light (e.g., 690 nanometers and 830 nanometers) can be emitted from the emitter(s), and the detector(s) detect light at the wavelengths produced by the emitter(s).

As shown in FIG. 8, the sensor panel 800 may further comprise pressure sensors, in addition to oximeter sensor units. In some situations, it may not be necessary to have pressure sensors in a sensor panel when there is good contact between the sensor panel and the entire tissue. In other situations, some portions of the tissue may not have good contact with a sensor panel, and oxygen saturation measured by the sensor panel from those portions may not be accurate. In these situations, a sensor panel including pressure sensors can be used to determine whether or not oxygen saturation readings from the tissue are accurate.

In FIG. 8, the sensor panel 800 includes pressure sensors 825*a*, 825*b*, and 825*c* in pixel elements 845*a*, 845*b*, and 845*c*, respectively, of the sensor panel 800. Each pressure sensor measures an amount of pressure that is applied on the sensor panel from different locations of the tissue. For example, the pressure sensor 825*a* measures an amount of pressure that is applied from the tissue location 835*a*. In another example, the pressure sensor 825*b* measures an amount of pressure that is applied from the tissue location 835*b*. In yet another example, the pressure sensor 835*c* measures an amount of pressure that is applied from the tissue location 835*c*. As described above, the pressure sensors can be a discrete set of sensors that are electrically connected to oximeter sensor units. Alternatively, the pressure sensors can be an electroactive multilayered fabric which is electrically connected to the oximeter sensor units.

In each pixel element of the sensor panel 800, an oximeter sensor unit is located adjacent to its respective pressure sensor. For each location of the tissue, a user can read both pressure applied by the tissue on the sensor panel, as well as oxygen saturation of the tissue at the same location. Both pressure and oxygen saturation readings from each pixel element of the sensor panel 800 can be transmitted to the system unit 805. If pressure measurements indicate that there is not good contact between a pixel element of the sensor panel and its corresponding tissue location, then oxygen saturation measured in the same pixel element can be ignored. On the other hand, if pressure measurements indicate that there is good contact between a pixel element of a sensor and its corresponding tissue location, then oxygen saturation measured in the same pixel element will be further processed by the system unit 805.

After the oxygen saturation measurement is successfully made, the processor 804 can also calculate whether the oxygen saturation value at each of the tissue locations is above or below a predetermined safety value. A predetermined safety value or an acceptable range of oxygen saturation may be selected by the user. It can also be preset by the factory or programmable by a user so that different predetermined safety values can be selected depending on the tissue type or the locations of the tissue. Then the system unit 805 can communicate with an output unit 818 to provide an output signal. Typically, when the oxygen saturation values measured from the sensor panel are above the predetermined safety value, then no output may be provided. If any of the oxygen saturation values is below the predetermined safety value, then the processor 804 communicates with the output unit 818 to provide an output signal. In some situations, it may be desirable to provide an output signal even when the oxygen saturation values measured from the sensor panel are above the predetermined safety value. In these situations, different types of output signals (e.g., flashing lights in different colors) can be provided so that a user can discern which locations of the tissue meet or do not meet the predetermined safety value for oxygen saturation.

A wide variety of output signals can be provided by the output unit 818. In FIG. 8, although the output unit 818 is shown to be located at the system unit 805, it can be located at the sensor panel 800, or at both places.

In one embodiment, the output unit 818 can provide an audible signal by a speaker or an alarm. If any of the oxygen saturation values measured from the sensor panel 800 falls below the predetermined safety value, then the output unit 818 can provide an audible signal. In this instance, the output unit 818, which can be a speaker or an alarm, can be located at the system unit 805 (e.g., a portable console) or at the sensor panel 800. In situations where the entire system (including the sensor panel and the system unit) is integrated into a product, e.g., a bed sheet or a garment, it may be desirable to use a simple output unit such as an alarm to reduce the overall bulkiness or volume of the product.

Alternatively or additionally, the output unit 818 can provide a visual signal. The visual signal can be a simple flashing light on the system unit 805 (e.g., on a portable console) or on the sensor panel 800 when any of oxygen saturation values measured from oximeter sensor units falls below a predetermined safety value.

The visual signal can also be provided on a display monitor on the system unit 805. The display monitor can show, graphically or numerically, oxygen saturation values measured from the oximeter sensor units in the sensor panel 800, as well as the locations of the tissue from which the values are measured. For simplicity, the display monitor can show oxygen saturation values and their locations only when the values fall below a predetermined safety value.

In some situations, however, it may be desirable to display oxygen saturation values for the locations of the tissue. In this instance, rather than showing numerical values for the locations on the monitor, it may be simpler to assign different colors for certain ranges of oxygen saturation values and then display different colors on the monitor. For example, if a measured oxygen saturation value is between 70 and 100 percent, then this value is displayed as a green dot on the monitor. If a measured oxygen saturation value is between 30 and 70 percent, then this value is displayed as a yellow dot on the monitor. If a measured oxygen saturation value falls below 30 percent, then this value is displayed as a red dot on the monitor. Since the locations in the tissue are color coded according to the oxygen saturation ranges, a user can readily identify an area in the tissue where the oxygenation state is less than optimal.

In another embodiment, the output unit 818 is a visible light source, such as LEDs, located at the sensor panel 800. By providing an output signal directly on the sensor panel 800, a user can immediately visualize where a problem may reside in a tissue, without having to rely on a display monitor that is located some distance away from a tissue.

One example of an output unit that can provide a visual signal on the sensor panel 800 is a visible light source, such as LEDs. The LEDs that emit visible light can be connected to each pixel 845*a*, 845*b*, and 845*c* of the sensor panel 800. The LEDs are electrically connected to the system unit 805, by wires or cables, so that they can be activated under certain conditions determined by the system unit 805. The LEDs are placed on a nontissue facing surface of the sensor panel, on the opposite side of oximeter sensor units that are located on a tissue facing surface of the sensor panel 800. Therefore, the LEDs are visible to the user even when the sensor panel 800 is placed on the tissue.

Any one of the LEDs can be lit as a warning when any oxygen saturation values measured from the pixel elements fall below a predetermined safety value. For example, if the processor 804 calculates that oxygen saturation values measured at tissue locations 835*a* and 835*c* are below the predetermined safety value, then the processor 804 will send a signal to the LEDs located at pixel elements 845*a* and 845*c* to light up. The LEDs are available in different colors (e.g., red, blue, green, violet, orange, yellow, or white), and any one or more colored LEDs can be connected to the sensor panel 800. Since the sensor panel is applied on a target tissue, a user can immediately visualize which location of the target tissue is compromised in terms of oxygenation.

In yet another embodiment, the output unit 818 can be a marker or markers that are located at the sensor panel 800, and the marker can provide a visible mark (e.g., ink) directly on the tissue based on oxygen saturation values. The markers can be connected to each pixel element of the sensor panel 800, and the markers are connected to a marker source (e.g., an ink source) which is electrically connected and controlled by the system unit 805. The marker can drop, spray, or stamp the tissue with an ink of any color choice. A mark is made when the oxygen saturation measurement is low, and no mark is made when the oxygen saturation measurement is satisfactory. When it is desired, oxygen saturation ranges can be color coded as described above, and the tissue can be marked with different color ink at various locations of the tissue, depending on the oxygen saturation value measured from each location. Then the user can readily visualize on the tissue itself, where the oxygen saturation is acceptable, and where is not acceptable.

As described above, various components shown in FIG. 8 can be combined together to provide a system that can provide oxygen saturation measurements (and pressure measurements in some embodiments) for various locations of a tissue simultaneously. The system described above can be used to monitor the oxygenation state of a large tissue, even a tissue that is highly contoured.

VIII. Applications and Methods for Providing Output Based on Oxygen Saturation

Embodiments of the invention have many applications. For example, embodiments of the invention can be applied in monitoring tissue viability during or after plastic surgery. In another example, they can also be used to estimate healing potentials of grafted tissues. Embodiments of the invention can be applied whenever it is suspected that the oxygenation state of a tissue is unstable.

One particular application of embodiments of the invention is in diagnosing whether a patient is at risk of developing pressure ulcers. Pressure ulcers, also known as decubitus ulcers, are localized damage to the skin and its underlying tissue caused by pressure, friction, shear, moisture, or any combination of these factors. Pressure ulcers are pressure injuries which produce open sores in the skin, but can extend to underlying structures such as muscle and bone. Pressure ulcers can be painful, and can lead to serious complications, such as blood poisoning and bone infections.

Pressure ulcers can develop in any area of the body. In adults, the damage usually occurs over bony prominences, such as the sacrum or where there is too much pressure on the skin and its underlying tissue due to their own weight. People can prevent pressure ulcers by changing body positions or by moving around. However, when a person is generally immobile due to a medical condition (e.g., stroke or coma), the person is at a higher risk of developing pressure ulcers.

A doctor or caretaker can routinely check patients for early signs of pressure ulcers, such as skin redness. However, visual inspections alone may not be sufficient to detect skin redness and other visual indicators of pressure ulcers, especially in patients with dark pigmented skin. Moreover, deep tissue injuries underlying the skin cannot be detected by visual inspections, until they lead to other serious complications.

Embodiments of the invention can be applied as a diagnostic tool for detecting pressure ulcer development at an early stage, as it can be used to measure oxygen saturation of tissues underlying the skin. In this application, a sensor panel or a sensor panel array can be incorporated into a bed sheet or a garment that can be worn by a patient. The patient can lie down on the bed sheet or wear the garment. The sensor panel (or the sensor panel array) can be positioned within the bed sheet or the garment, such that any locations of the patient's body that are under constant pressure can be monitored for oxygen saturation. If oxygen saturation measured from any location of the body falls below a predetermined safety value, then a caretaker can be alerted so that an appropriate treatment can be administered in a timely manner. A treatment may simply be turning the patient's body and relieving pressure from certain parts of the body.

Figure 9:
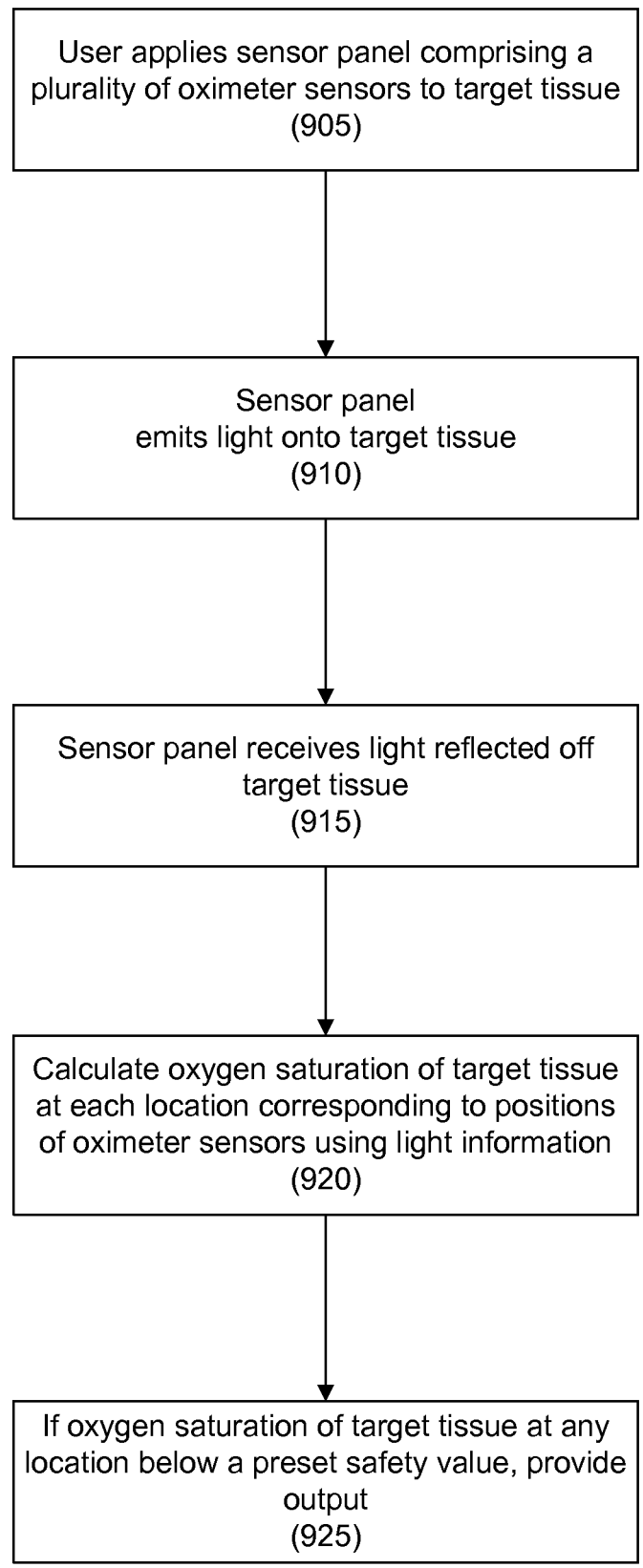
FIG. 9 shows a flow diagram for a method of using a sensor panel to determine oxygen saturation of a target tissue and to determine whether to provide an output signal.
Figure 10:
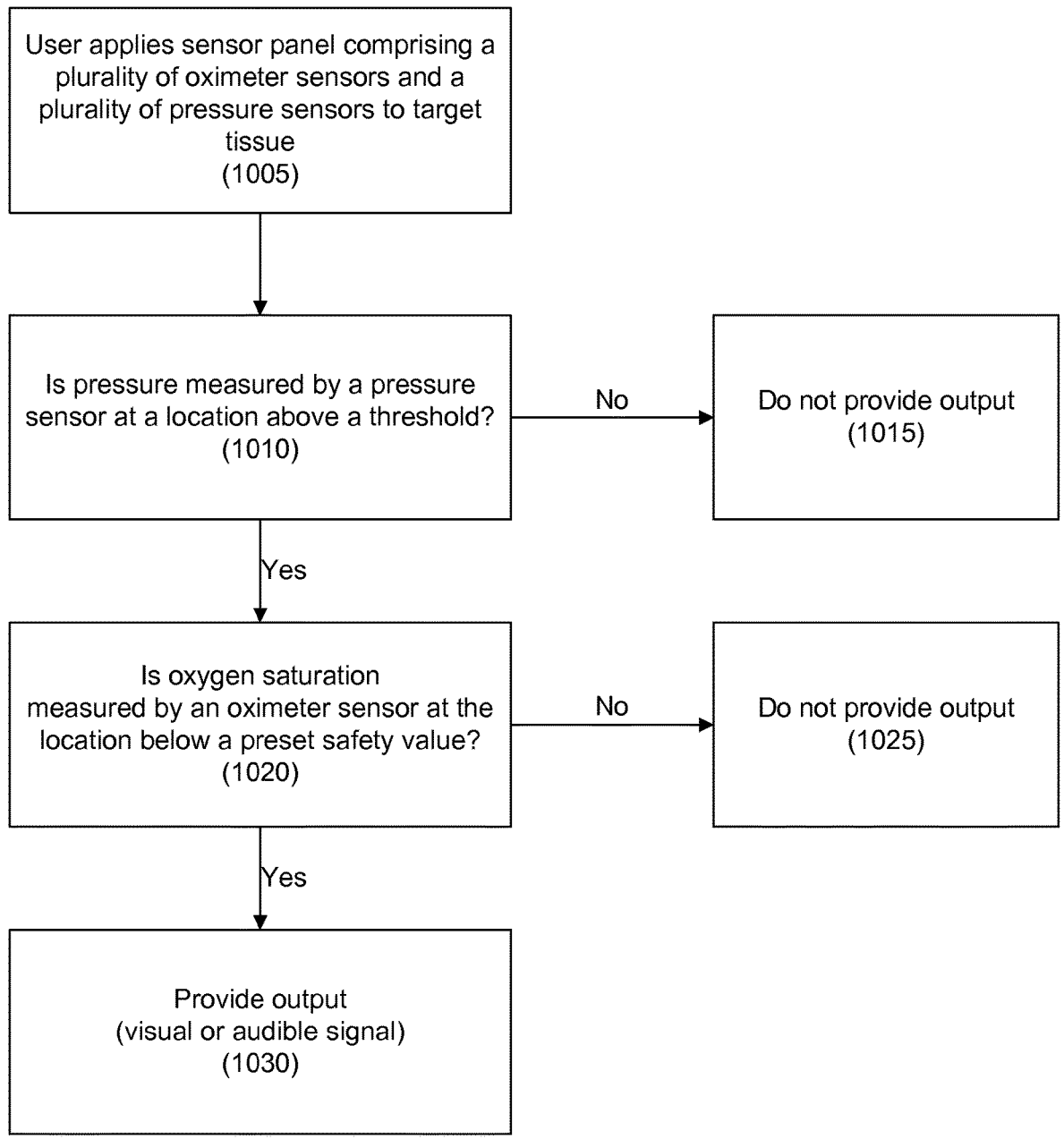
FIG. 10 shows a flow diagram for another method of using a sensor panel to measure oxygen saturation of a target tissue and pressure applied by the target tissue and to determine whether to provide an output signal.

The methods for measuring oxygen saturation in a tissue are described in FIGS. 9 and 10, and these methods can be used to diagnose whether a person is at risk of developing pressure ulcers or any other conditions where tissue oxygenation state is unstable.

FIG. 9 is a flow diagram that shows a process of determining oxygen saturation of a tissue using a sensor panel and providing an output signal based on the measured oxygen saturation and a predetermined safety value.

First, in step 905, a user (e.g., a doctor) applies, to a target tissue, a sensor panel including a flexible substrate and oximeter sensor units. Typically, the sensor panel is applied to the surface of the skin in order to measure the oxygen saturation of a particular tissue.

In step 910, when the sensor panel touches or is in contact with the target tissue, a system unit directs an emitter to transmit light to the target tissue. After the light is transmitted into the target tissue, some of the light is reflected off of the tissue.

In step 915, a detector detects the light reflected off of the target tissue. Then, this light information is sent to the system unit.

In step 920, a processor in the system unit calculates the oxygen saturation of the target tissue at each location of the tissue corresponding to positions of oximeter sensor units in the sensor panel using this light information. The computer also compares each oxygen saturation value with a predetermined safety value.

A predetermined safety value for oxygen saturation of a tissue can be set at, for example, 30, 40, 50, 60, 70, 80, 90, 95, 99, or 100 percent, or any other percent numbers in between. For example, if the predetermined safety value is set at 30 percent and if an oxygen saturation value measured from a location in a tissue is 27 percent, then the oxygen saturation value is considered to be below the predetermined safety value. In some situations, a predetermined safety value may be set as a range of values, rather than a single point value. For example, a predetermined safety value can be set as a range of 60 to 99 percent as an acceptable range of oxygen saturation. The selection of the predetermined safety value depends on clinical situations. For example, during a skin graft surgery, the predetermined safety value for oxygen saturation may be set at, e.g., 30 percent as an acceptable level for a detached skin flap. However, to monitor whether the grafted skin is stable after surgery, the predetermined safety value may be set higher, e.g., at 60 percent.

In some embodiments, a predetermined safety value or an acceptable range for oxygen saturation of a tissue can be set differently for different regions of the sensor panel. For example, a predetermined safety value measured from oximeter sensor units located at a center area of the sensor panel can be set higher (e.g., at 60 percent), and a predetermined safety value measured from oxygen sensor units located at edges of the sensor panel can be set lower (e.g., at 35 percent). In another example, a predetermined safety value for oximeter sensor units located at a higher density area of oximeter sensor units can be set higher than a predetermined safety value for oximeter sensor units located at a lower density area of oximeter sensor units. Some areas in a tissue may require a higher threshold for oxygen saturation, where another area in the same tissue may require a lower threshold for oxygen saturation for the entire tissue to function properly. Thus, it would be useful to have a sensor panel with sensitivities of oximeter sensor units set individually or by groups to handle a tissue with areas of different oxygen saturation requirements.

In Step 925, the system unit communicates with an output unit to provide an output signal. When the oxygen saturation values measured from the sensor panel are above a predetermined safety value, then no output signal may be provided. However, if any one of the oxygen saturation values measured from the sensor panel is below the predetermined safety value, then an output is provided. As described above and in FIG. 8, a number of different types of audible and visual output signals can be provided to alert a doctor or a caretaker.

For simplicity, it is described in step 925 that output is provided only if oxygen saturation of any location of the target tissue is below a predetermined safety value. If desired, however, an output can also be provided if oxygen saturation is above the predetermined safety value. In this instance, the output signal when the oxygen saturation is above the predetermined safety value should be distinguishable from the output signal when the oxygen saturation is below the predetermined safety value.

FIG. 10 is a flow diagram that shows a process of determining oxygen saturation of a tissue using a sensor panel including a flexible substrate and oximeter sensor units and pressure sensors, connected to the flexible substrate. An output signal is provided based on the measured oxygen saturation and pressure from the sensor panel.

In step 1005, a user applies to a target tissue, a sensor panel including a flexible substrate including oximeter sensor units and pressure sensors, connected to the flexible substrate.

In step 1010, the pressure sensors measures the pressure that is applied on the sensor panel by the target tissue. Then a processor in a system unit determines whether there is good contact between the sensor panel and the target tissue by comparing the measured pressure to a threshold value. The threshold value depends on many factors including, for example, a patient's distributed weight over the tissue surface. For example, the threshold value can be set at 0.5, 1, 5, or 10 kilograms. The threshold value can also be set as a range, rather than a point value. For example, the threshold can be set as a range between about 0.5 to 1 kilograms, 1 to 10 kilograms, an so forth. The threshold value can also be a relative pressure (comparing pressure measured from different areas of a tissue), rather than an absolute pressure measurement.

In step 1015, if the pressure measured from the sensor panel is below a threshold, then this indicates that the sensor panel and the target tissue do not have good contact. In such a case, an oxygen saturation value measured at that location may be inaccurate, and the system unit may ignore the oxygen saturation value and provide no output.

In Step 1020, if it is determined that the pressure measured from the sensor panel is above the threshold, then the processor in the system unit analyzes the oxygen saturation measured from the same location in the tissue.

In step 1025, if the oxygen saturation measured from the same location in the tissue is above a predetermined safety value, typically, no output is provided.

In step 1035, if the oxygen saturation measured from the same location in the tissue is below the predetermined safety value, then a number of different types of audible and visual output signals can be provided to alert the doctor as described above.

In FIG. 10, while the pressure applied to the tissue is measured in step 1010 and the oxygen saturation is measured at step 1020, the order of these two steps can be reversed or can be performed simultaneously.

The processes shown in FIGS. 9 and 10 are useful in diagnosing pressure ulcer development and other conditions involving unstable tissue oxygenation. Since embodiments of the invention allow examination of a relatively large area of a body and tissues underlying the skin for oxygenation state, a doctor can monitor and catch a patient at an earlier stage of pressure ulcer development or other diseased state. Prognosis for early-stage pressure ulcers is excellent with timely appropriate treatment. Embodiments of the invention contribute, among other things, in solving the problems related to a diagnosis of pressure ulcer development, as well as improving oxygen saturation measurements from a large, contoured surface of a body and tissues.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:
1. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the plurality of oximeter sensors are arranged in an irregular grid, in which rows are formed from nonstraight lines that are not parallel to one another and columns are formed from nonstraight lines that are not parallel to one another.

2. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the oximeter sensor units in the plurality of oximeter sensor units are grouped in a pattern, and the oximeter sensor units in the plurality of oximeters are grouped together so that the oximeter sensor units are unevenly distributed throughout the sensor panel.

3. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the flexible substrate comprises a first side and a second side,
the plurality of oximeter sensor units are coupled to the second side of the flexible substrate,
the second side of the flexible substrate faces tissue to be measured by the plurality of oximeter sensor units,
the second side of the flexible substrate does not include an adhesive that is used to attach the sensor panel to the tissue to be measured, and
the oximeter sensor units are sewn into the flexible substrate.

4. A system comprising:
a sensor panel comprising:
a flexible substrate; and a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the flexible substrate comprises a first side and a second side,
the plurality of oximeter sensor units are coupled to the second side of the flexible substrate,
the second side of the flexible substrate faces tissue to be measured by the plurality of oximeter sensor units,
the second side of the flexible substrate does not include an adhesive that is used to attach the sensor panel to the tissue to be measured, and
the oximeter sensor units are woven into the flexible substrate.

5. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the sensor panel is arranged in rows and columns,
a first position in a first row and first column comprises a first oximeter sensor unit;
a second position in the first row and second column comprises a second oximeter sensor unit; and
a third position in a second row and second column does not comprise an oximeter sensor unit.

6. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the sensor panel is arranged in rows and columns,
a first position in a first row and first column comprises a first oximeter sensor unit;
a second position in the first row and a second column does not comprise an oximeter sensor unit; and
a third position in the first row and a third column comprises a second oximeter sensor unit.

7. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the plurality of oximeter sensor units are arranged on the out most boundary of the sensor panel.

8. A system comprising:
a sensor panel comprising:
a flexible substrate; and
a plurality of oximeter sensor units coupled to the flexible substrate,
wherein each oximeter sensor unit comprises a first source structure and a first detector structure;
a first multiplexer, coupled along a first axis of the plurality of oximeter sensor units coupled to the flexible substrate; and
a second multiplexer, coupled along a second axis of the plurality of oximeter sensor units coupled to the flexible substrate,
wherein the plurality of oximeter sensor units are arranged with a higher density near a center of the sensor panel.

* * * * *